US005677296A

United States Patent [19]

Chrusciel et al.

[11] Patent Number: 5,677,296

[45] Date of Patent: Oct. 14, 1997

[54] CARBAMIC ACID DERIVATIVES OF SUBSTITUTED DIBENZOXAZEPINE COMPOUNDS, PHARMACEUTICAL COMPOSITIONS AND METHODS OF USE

[75] Inventors: Robert Alan Chrusciel, Portage, Mich.; Timothy Joseph Hagen, Gurnee; E. Ann Hallinan, Evanston, both of Ill.; Jinglin Li, St. Louis, Mo.; Sofya Tsymbalov, Des Plaines, Ill.; David B. Reitz, Chesterfield, Mo.

[73] Assignee: G.D. Searle & Co., Chicago, Ill.

[21] Appl. No.: 446,193

[22] Filed: May 19, 1995

Related U.S. Application Data

[62] Division of Ser. No. 147,356, Nov. 3, 1993, Pat. No. 5,488,046.

[51] Int. Cl.$^6$ .................... A61K 31/55; C07D 498/04; C07D 513/04

[52] U.S. Cl. .................... 514/211; 540/578

[58] Field of Search .................... 514/211; 540/578

[56] References Cited

U.S. PATENT DOCUMENTS

| | | | |
|---|---|---|---|
| 2,852,528 | 9/1958 | Hoffmann et al. | 260/327 |
| 3,210,372 | 10/1965 | Werner et al. | 260/309.6 |
| 3,357,998 | 12/1967 | Cusic et al. | 260/333 |
| 3,534,019 | 10/1970 | Coyne et al. | 260/239 |
| 3,624,104 | 11/1971 | Cusic et al. | 260/333 |
| 3,809,698 | 5/1974 | Yale et al. | 260/268 |
| 3,856,781 | 12/1974 | Yale et al. | 260/240 |
| 3,856,782 | 12/1974 | Yale et al. | 260/240 |
| 3,875,166 | 4/1975 | Yale et al. | 260/288 |
| 3,917,649 | 11/1975 | Mueller | 260/333 |
| 3,989,719 | 11/1976 | Mueller | 260/333 |
| 3,992,375 | 11/1976 | Mueller | 260/240 |
| 4,045,442 | 8/1977 | Mueller | 260/293.58 |
| 4,125,532 | 11/1978 | Mueller | 260/244.4 |
| 4,170,593 | 10/1979 | Mueller | 260/243.3 |
| 4,290,953 | 9/1981 | Koizumi et al. | 260/333 |
| 4,360,525 | 11/1982 | Müller . | |
| 4,379,150 | 4/1983 | Ito et al. | 424/244 |
| 4,559,336 | 12/1985 | Mueller | 514/211 |
| 4,559,337 | 12/1985 | Mueller | 514/211 |
| 4,614,617 | 9/1986 | Mueller | 540/547 |
| 4,681,939 | 7/1987 | Mueller | 540/547 |
| 4,704,386 | 11/1987 | Mueller | 514/211 |
| 4,888,335 | 12/1989 | Mohrbacher et al. | 514/217 |
| 5,180,720 | 1/1993 | Husa et al. | 514/211 |
| 5,182,272 | 1/1993 | Hallinan et al. | 514/211 |
| 5,212,169 | 5/1993 | Husa et al. | 514/211 |
| 5,225,417 | 7/1993 | Dappen et al. | 514/279 |
| 5,281,590 | 1/1994 | Husa et al. | 514/211 |
| 5,283,240 | 2/1994 | Hallinan et al. | 514/80 |
| 5,288,719 | 2/1994 | Husa et al. | 514/211 |
| 5,304,644 | 4/1994 | Husa et al. | 540/547 |
| 5,324,722 | 6/1994 | Hagen et al. | 514/211 |
| 5,354,746 | 10/1994 | Chandrakumar et al. | 514/211 |
| 5,354,747 | 10/1994 | Hansen et al. | 514/211 |
| 5,354,863 | 10/1994 | Dappen et al. | 546/35 |
| 5,395,932 | 3/1995 | Chandrakumar et al. | 540/547 |

FOREIGN PATENT DOCUMENTS

| | | | |
|---|---|---|---|
| 0012385 | 6/1980 | European Pat. Off. | C07D 267/20 |
| 0193822 | 9/1986 | European Pat. Off. | C07D 267/20 |
| 0218077 | 4/1987 | European Pat. Off. | C07D 267/20 |
| 0480641 | 4/1992 | European Pat. Off. | C07D 223/20 |
| 0534667 | 3/1993 | European Pat. Off. | C07D 417/06 |
| 6700603 | 7/1967 | Netherlands . | |
| 1170322 | 11/1969 | United Kingdom | C07D 87/54 |
| 1331892 | 9/1973 | United Kingdom | C07D 87/54 |
| 1522003 | 8/1978 | United Kingdom . | |
| WO92/19617 | 11/1992 | WIPO | C07D 413/12 |
| WO93/07132 | 4/1993 | WIPO | C07D 267/20 |
| WO93/09104 | 5/1993 | WIPO | C07D 267/20 |

OTHER PUBLICATIONS

A. Bennett, et al. "Antagonism of Prostanoid–Induced Contractions of Rat Gastric Fundus Muscle by SC–19220 Sodium Meclofenamate, Indomethacin or Trimethoquinol," *Br. J. Pharmac.*, 71, 169–175 (1980)—London.

W.E. Coyne, et al. "Anticonvulsant Semicarbazides," *J. Med. Chem.*, 11(6), 1158–1160 (1968)—USA.

E.J. Drower, et al. "The Antiociceptive Effects of Prostaglandin Antagonists in the Rat, "*European Journal of Pharmacology*, 133, 249–256 (1987)—Europe.

F.R. George, et al. "Antagonism of Alcohol Hypnosis by Blockade of Prostaglandin Synthesis and Activity: Genotype and Time Course Effects," *Pharmacology, Biochemistry & Behavior*, vol. 19, 131–136 (1983)—USA.

(List continued on next page.)

*Primary Examiner*—Robert T. Bond

*Attorney, Agent, or Firm*—Fitzpatrick, Cella, Harper & Scinto

[57] ABSTRACT

The present invention provides substituted dibenzoxazepine compounds of Formula I:

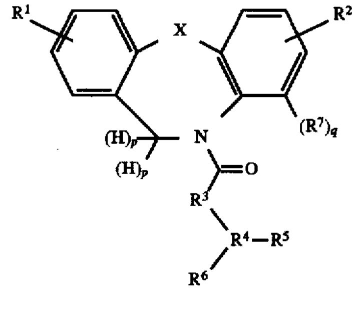

which are useful as analgesic agents for the treatment of pain, and as prostaglandin-$E_2$ antagonists for the treatment of prostaglandin-$E_2$ mediated diseases, pharmaceutical compositions comprising a therapeutically-effective amount of a compound of Formula I in combination with a pharmaceutically-acceptable carrier, a method for eliminating or ameliorating pain in an animal, and a method for treating prostaglandin-$E_2$ mediated diseases in an animal, comprising administering a therapeutically-effective amount of a compound of Formula I to the animal.

28 Claims, No Drawings

OTHER PUBLICATIONS

R. Gimet, et al. "Quantitative Determination of Polymorphic Forms in a Formulation Matrix Using the Near Infra-Red Reflectance Analysis Technique," *Journal of Pharmaceutical & Biomedical Analysis*, vol. 5, No. 3, 205-211 (1987)—Great Britain.

A. Gomes, et al. "Pharmacodynamics of Venom of the Centipede *Scolopendra Subspinipes Dehaani*," *Indian Journal of Experimental Biology*, vol. 20, 615-618, Aug. (1982)—India.

K. Gyires, et al. "The Use of the Writhing Test in Mice for Screening Different Types of Analgesics," *Arch. Int. Pharmacodyn*, 267, 131-140 (1984)—USA.

D.E. MacIntyre, et al. "Antagonism of Human Platelet Responses to Stimulatory and Inhibitory Prostaglandins," *Prog. Lipid. Res.*, 20(1-4), 453-9 (1981)—USA.

C.A. Maggi, et al. "The Effect of SC-19220, a Prostaglandin Antagonist, on the Micturition Reflex in Rats," *European Journal of Pharmacology*, 152, 273-279 (1988)—Europe.

K. Nagarajan, et al. "Synthesis of 10,11-Dihydrodibenz[b,f][1,4]oxazepine Derivatives as Potential Anticonvulsant & Psychotropic Agents," *Indian Journal of Chemistry*, vol. 24B, 840-844 (1985)—India.

S. Nakajyo, et al. "Inhibitory Effect of Bassianolide, a Cyclodepsipeptide, on Drug-Induced Contractions of Isolated Smooth Muscle Preparations," *Japan J. Pharmacol.*, 32, 55-64 (1982)—Japan.

A. Rakovska, et al. "Antagonistic Effect of SC-19220 on the Responses of Guinea-Pig Gastric Muscles to Prostaglandins $E_1$, $E_2$, and $F_{2\alpha}$," *Arch. Int. Pharmacodyn.*, 268, 59-69 (1984)—USA.

J.H. Sanner "Dibenzoxazepine Hydrazides as Prostaglandin Antagonists," *Intra-Science Chem. Rept.*, vol. 6, No. 1, 1-9 (1972)—USA.

J.H. Sanner, et al. "Structure-Activity Relationships of Some Dibenzoxazepine Derivatives as Prostaglandin Antagonists," *Advances in the Biosciences*, 9, 139-148 (1972)—USA.

U.S. application No. 07/813,316, Hagen et al., filed Dec. 20, 1991.

U.S. application No. 08/126,826, Husa et al., filed Sep. 24, 1993.

U.S. application No. 08/133,681, Chandrakumar et al., filed Oct. 7, 1993.

U.S. application No. 08/134,345, Chandrakumar et al., filed Oct. 7, 1993.

CARBAMIC ACID DERIVATIVES OF SUBSTITUTED DIBENZOXAZEPINE COMPOUNDS, PHARMACEUTICAL COMPOSITIONS AND METHODS OF USE

This is a Divisional Application of application Ser. No. 08/147,356, filed on Nov. 3, 1993 now U.S. Pat. No. 5,488,046.

BACKGROUND OF THE INVENTION (1) Field of the Invention

The present invention generally relates to compounds having pharmacological activity which are useful as pharmaceutical agents and, more particularly, as analgesic agents for the treatment of pain, and as prostaglandin-$E_2$ antagonists for the treatment of prostaglandin-$E_2$ mediated diseases, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and medical methods of treating pain and prostaglandin-$E_2$ mediated diseases employing these compounds.

Analgesic compounds are agents which alleviate pain without causing a loss of consciousness and, thus, which are useful for treating pain.

The major classes of analgesic compounds include narcotic analgesics, or opiates, compounds which alleviate pain and induce sleep, and analgesic-antipyretic compounds, compounds which alleviate pain and reduce fever and inflammation, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor salicylates, and represent another class of compounds which are useful as analgesic agents.

(2) Description of the Related Art

U.S. Ser. No. 08/079,021 discloses 2-, 3-, 4-, 5-, 6-, 7-, 8-, 9- and/or 10-Substituted Dibenzoxazepine and Dibenzthiazepine Compounds, Pharmaceutical Compositions and methods for treating pain and prostaglandin-$E_2$ mediated diseases.

U.S. Pat. No. 3,357,998 discloses derivatives of dihydrodibenz[b,f][1,4]oxazepine-10-carboxylic acids.

U.S. Pat. No. 4,170,593 discloses 1-(substituted amino) alkanoyl-2-(dibenzoxazepine-10-carbonyl) hydrazines and derivatives thereof.

U.S. Pat. No. 4,681,939 discloses 8-chlorodibenz-[b,f][1, 4]oxazepine-10(11H)carboxylic acid, 2-[(substituted phenylsulfinyl)alkanoyl]hydrazides and 8-chlorodibenz[b,f] [1,4]oxazepine-10(11H)-carboxylic acid, 2-[(substituted phenylsulfonyl)alkanoyl]hydrazides.

U.S. Pat. No. 3,856,782 discloses 2-benzyl-3H,7H-quino (8,1-cd)(1,5)benzoxazepin-3-one compounds.

U.S. Pat. No. 3,856,781 discloses 2-pyridylmethyl-3H, 7H-quino(8,1-cd)(1,5)benzoxazepin-3-one compounds.

U.S. Pat. No. 3,809,698 and U.S. Pat. No. 3,875,166 disclose 3-(aminoalkoxy)-2,3-dihydroquinobenzoxa(or thia) zepine derivatives.

U.S. Pat. No. 3,534,019 discloses compounds which are hydrazides of tricyclic N-carboxylic acids.

U.S. Pat. No. 4,379,150 discloses dibenz[b,f][1,4] oxazepine derivatives which may have a heterocyclic ring present in the side chain at the 10-position of the molecule.

U.S. Pat. No. 2,852,528 discloses 11-unsubstituted 10-(tertiary aminoalkyl)-dibenzo-[b:f]-thia-[1]-aza-[4]-cycloheptadiene-[2:6] compounds.

6B 1 522 003 discloses 1-acyl-2-(8-chloro-10,11-dihydrodibenz[b,f][1,4]oxazepine-10-carbonyl)hydrazines.

European Patent Application Publication No. 0 480 641 A1 discloses tricyclic heterocycles which are stated to have anti-hyperalgesic properties.

European Patent Application Publication No. 0 534 667 A1 discloses tricyclic heterocycles which are stated to counteract mild to moderate pain by virtue of their anti-hyperanalgesic properties.

K. Nagarajan et al. in "Synthesis of 10,11-Dihydrodibenz [b,f][1,4]oxazepine Derivatives as Potential Anticonvulsant and Psychotropic Agents," *Indian Journal of Chemistry*, 24B, 840–844 (1985), disclose several acyl, carbamoyl and thiocarbamoyl derivatives of 10,11-dihydrodibenz[b,f][1,4] oxazepine.

William E. Coyne et al. in "Anticonvulsant Semicarbazides," *J. Med Chem.* 11(6), 1158–60 (1968) disclose 10,11-dihydrodibenz[b,f][1,4]oxazepine-10-carboxylic acid hydrazides.

Each of the documents described hereinabove discloses compounds which are structurally different from the compounds of the present invention. Thus, the compounds of the present invention are structurally distinct from that which has been described in the art.

SUMMARY OF THE INVENTION

The present invention provides compounds having a structure of Formula I:

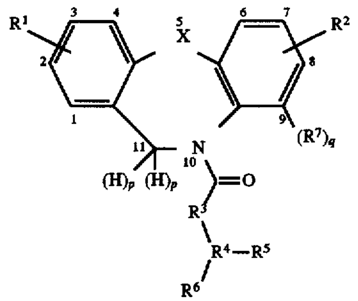

or a pharmaceutically-acceptable salt thereof, wherein:

X is oxygen, sulfur,

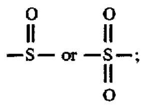

$R^1$, $R^2$ and $R^7$ may be the same or different and are hydrogen or halogen;

$R^3$ is oxygen,

—NH—, —N-alkyl, —N-aryl, —N-alkylenearyl or —N—, and can combine with $R^4$ and $R^5$ to form

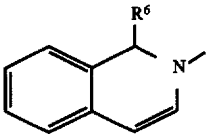 or 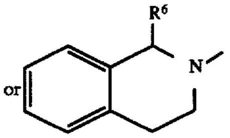 ;

$R^4$ is carbon or —CH—, and can combine with $R^5$ to form carbonyl, a 4-, 5- or 6-membered nonaromatic, saturated, single-ring structure,

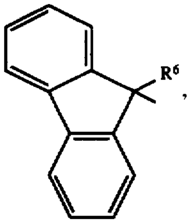 ,

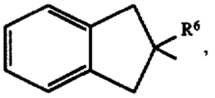 ,

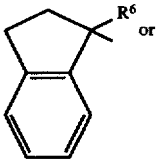 or

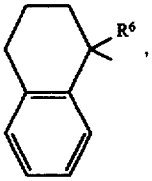 , and can combine with $R^3$ and $R^8$ to form

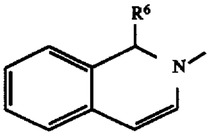 or 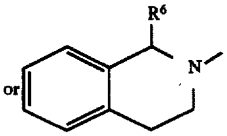 ;

$R^5$ is $—(CH_2)_m—$, oxygen, aryl, aralkyl, arylcarbonylhydroxy, arylcarbonylalkoxy, a mono- or di-valent alkylenearyl or a mono- or divalent alkenylenearyl, and can combine with $R^4$ to form carbonyl, a 4-, 5- or 6-membered nonaromatic, saturated, single-ring structure,

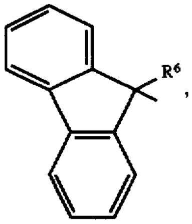 ,

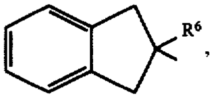 ,

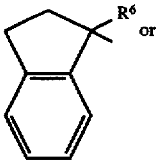 or

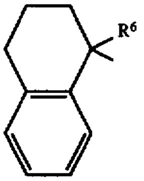 , and can combine with $R^3$ and $R^4$ to form

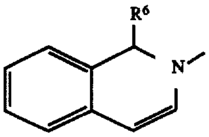 or 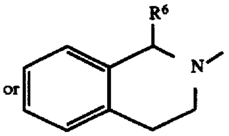 ;

$R^6$ is a single covalent bond to the carbon 9 of said compound, or a single or double covalent bond to the carbon 11 of said compound;

p and q may be the same or different, and are 0 or 1; and m is 3, 4 or 5;

with the proviso that $R^2$ cannot be at the carbon 9 position of said compound.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal, or for treating a prostaglandin-$E_2$ mediated disease, comprising administering a therapeutically-effective amount of a compound of Formula I to the animal.

DETAILED DESCRIPTION OF THE INVENTION

(1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The symbols ▼ and ▽ as used herein denote one of two possible stereoisomers, with the symbol ▼ indicating outside of the plane, but in front of the plane, and the symbol ▽ indicating outside of the plane, but behind the plane.

Many of the compounds which are shown and/or described in the "Examples" Section of this specification are referred to by a bolded whole number. This method of referring to these compounds is conventional, and is understood by those of skill in the art. These compounds have the chemical name stated, and the structure which is shown, where they first appear in the specification. For example, 1 has the chemical name and structure which appears for Compound 1 in Example 1.

The abbreviations "AcOH" and "HOAc" as used herein mean acetic acid.

The term "alkyl" as used herein means a saturated hydrocarbon radical having from one to ten carbon atoms, and within which includes from one to six carbon atoms, and further within which includes one, two or three carbon atoms, which can be a straight or branched chain. Representative of such radicals are methyl, ethyl, propyl, isopropyl, butyl, sec-butyl, isobutyl, tert-butyl, pentyl and the like.

The term "alkenylene" as used herein means an alkylene group, as defined below, but which has one, two or three double bounds.

The term "alkylene" as used herein means a straight, branched or cyclic saturated hydrocarbon chain spacer arm which has from one to ten carbon atoms, and within which includes from one to six carbon atoms, and further within which includes one, two, three, four, five or six carbon atoms.

The term "alkylenearyl" as used herein means an alkylene group, as defined above, which has an aryl group, as defined below, attached to it on one end or, when the alkylene group is cyclic, on one or two of its sides. Examples of alkylenearyl groups include the following:

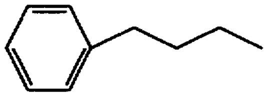
,

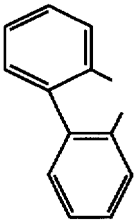
,

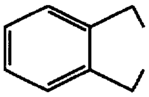
,

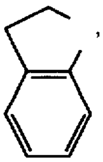
,

-continued

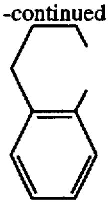

or

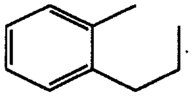
.

The term "alkenylenearyl" as used herein means an alkenylene group, as defined above, which has an aryl group, as defined below, attached to it on one end, or, when the alkenylene group is cyclic, on one or two of its sides. Examples of alkenylenearyl groups include the following:

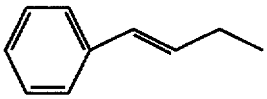
and
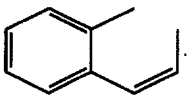
.

The abbreviation "$AlMe_3$" as used herein means trimethylaluminum.

The term "amino" as used herein means an $—NH_2$ group.

The term "analgesia" as used herein means the reduction, or absence, of sensibility to pain, designating particularly the relief of pain without loss of consciousness.

The term "animal" as used herein includes mammals and nonmammals, and further includes humans and nonhuman mammals.

The term "aryl" as used herein means 5- and 6-membered single-ring aromatic radicals which may include from zero to four heteroatoms, and within which includes from zero to two heteroatoms, and further within which includes from zero to one heteroatom, wherein such heteroatoms are oxygen, nitrogen or sulfur. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The term "aralkyl" as used herein means an aryl radical, as defined above, which may have from one to five alkyl radicals, as defined above, attached to its carbon atoms and/or heteroatoms, and within which includes one, two or three of such alkyl radicals.

The term "arylcarbonylalkoxy" as used herein means an aryl radical, as defined above, which has a

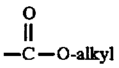

group attached to it, wherein alkyl is as defined above.

The term "arylcarbonylhydroxy" as used herein means an aryl radical, as defined above, which has a carboxy group, as defined below, attached to it.

The abbreviation "Boc" as used herein means t-butyloxycarbonyl.

The term "carbonyl" as used herein means a

group.

The term "carboxy" as used herein means a

group.

The term "composition" as used herein means a product which results from the combining of more than one element or ingredient.

The abbreviation "DMAP" as used herein means 4-(dimethylamino)pyridine.

The abbreviation "DMF" as used herein means dimethylformamide.

The abbreviation "DSC" as used herein means Differential Scanning Colorimetry.

The phrase "$EC_{50}$ concentration" as used herein means that concentration of a compound or drug which produces 50% of a maximal biological effect, such as contractions in isolated segments of guinea pig ileum.

The phrase "$ED_{50}$ dose" as used herein means that dose of a compound or drug which produced a biological effect, such as producing analgesia, in 50% of the animals to which the compound or drug was administered.

The abbreviation "DR" as used herein means dose ratio.

The abbreviation "Et" as used herein means ethyl ($-CH_2CH_3$).

The abbreviation "EtOAc" as used herein means ethyl acetate.

The abbreviation "EtOH" as used herein means ethanol ($CH_3CH_2OH$).

The abbreviation "$Et_3N$" as used herein means triethylamine.

The term "halo" or "halogen" as used herein means chlorine (Cl), bromine (Br), fluorine (F) and/or iodine (I).

The term "heteroatom" as used herein means an atom of any element other than carbon or hydrogen, such as oxygen, nitrogen or sulfur.

The abbreviation "$^1$H NMR" as used herein means Proton Nuclear Magnetic Resonance.

The abbreviation "HPLC" as used herein means High Pressure Liquid Chromatography.

The term "hydroxy" as used herein means the group —OH.

The term "intragastrically" and/or the abbreviation "i.g." as used herein mean that a compound or drug was administered into the stomach.

The abbreviation "i.p." as used herein means that a compound or drug was administered intraperitoneally.

The abbreviation "IR" as used herein means infrared (referring to an infrared spectrum).

The abbreviation "LAH" as used herein means lithium aluminum hydride.

The abbreviation "Me" as used herein means methyl ($-CH_3$).

The abbreviation "MeOH" as used herein means methanol ($CH_3OH$).

The abbreviation "mp" as used herein means melting point.

The abbreviation "MPLC" as used herein means Medium Pressure Liquid Chromatography.

The abbreviation "n-BuLi" as used herein means n-butyl lithium.

The abbreviation "NMR" as used herein means Nuclear Magnetic Resonance.

The abbreviation "n-Pr" as used herein means n-propyl.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laureate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laureate, benzoate, lactate, phosphate, tosylate, citrate, maleate, fumarate, succinate, tartrate, napsylate, clavulanate and the like salts, and alkali metal salts, such as sodium and potassium, and alkaline earth salts, such as calcium and magnesium.

The abbreviation "Pr" as used herein means propyl.

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy (Cbz), benzoyl and an L- or D-aminoacyl residue, which may itself be N-protected similarly.

The abbreviation "RaNi" as used herein means Raney nickel.

The abbreviation "s.c." as used herein means that a compound or drug was administered subcutaneously.

The abbreviation "t-Bu" as used herein means tert-butyl.

The abbreviation "TEA" as used herein means triethylamine.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product" and "title material" as used herein mean that compound, product or material whose chemical name is given, and/or whose structure is shown, in the particular example, or subpart thereof, referred to. If no particular example, or subpart thereof, is referred to, it means that compound, product or material whose chemical name is given, and/or whose structure is shown, in the particular example, or subpart thereof, in which it appears.

(2) Description of Invention

In one aspect, the present invention provides compounds comprising a structure of Formula I, as described above, and pharmaceutically-acceptable salts thereof.

The compounds of the present invention comprise a class of substituted dibenzoxazepine compounds in which the 1-, 2-, 3-, 4-, 5-, 6-, 7-, 8-, 9-, 10- and/or 11-position may be substituted.

Specific compounds within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans-geometric isomers, R- and S-enantiomers, diastereomers, d-isomers, l-isomers, the racemic mixtures thereof, and other mixtures thereof, as falling within the scope of the invention. For example, the following compounds are cis- and trans- geometric isomers: Compounds 3 and 4 of Example 2; Compounds 6 and 7 of Example 3; Compounds 9a and 9b of Example 4; Compounds 10 and 11 of Example 5; Compounds 14a and 14b of Example 7; Compounds 15a and 15b of Example 8; Compounds 16 and 17 of Example 9; Compounds 20a and 20b of Example 12; Compounds 26a and 26b of Example 18; and Compounds 27a and 27b of Example 19. Compounds 5a and 5b of Example 3 are enantiomers of Compound 5, and Compounds 6a and 6b of Example 3 are enantiomers of Compound 6. Additional asymmetric carbon atoms may be present in a substituent such as an alkyl group. All such isomers, as well as mixtures thereof, are intended to be included in this invention.

Certain compounds of the present invention may contain a basic functional group, such as amino, alkylamino or dialkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laureate, benzoate, lactate, phosphate, tosylate, citrate, maleate, fumarate, succinate, tartrate, naphthoate, mesylate, glucoheptonate, lactobionate, and laurylsulphonate salts and the like. (See, for example, S. M. Berge et al., "Pharmaceutical Salts," *J. Pharm. Sci.*, 66, 1–19 (1977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, or for producing some other therapeutic effect, as discussed in more detail hereinbelow, comprising administering a therapeutically-effective amount of a compound of Formula I, as described hereinabove, to the animal.

The preferred embodiments of this invention are Compound 5 (Example 3), Compound 5a (Example 3), Compound 5b (Example 3), Compound 6 (Example 3), Compound 6b (Example 3) and Compound 7 (Example 3). The most preferred embodiment of this invention is Compound 5 (Example 3).

(3) Utility

Compounds within the present invention have been found to exhibit activity as prostaglandin $E_2$ antagonists (antagonists of prostaglandins of the $E_2$ series).

Compounds within the present invention, and the pharmaceutical compositions comprising one or more of these compounds, are useful as analgesic agents for the elimination or amelioration of pain in animals.

In addition to treating pain, these compounds and compositions would be useful in treating prostaglandin-$E_2$ mediated diseases, such as convulsions, ischemia and other central nervous system disorders, as well as osteoporosis, dysmenorrhea, asthma, enuresis, arrhythmia, urinary incontinence, gastric hypermotility, irritable bowel syndrome and diarrhea, by virtue of their activity as prostaglandin $E_2$ antagonists.

(4) Methods of Preparation

In general, the compounds of the present invention may be prepared by the methods illustrated in the following general reaction schemes, or by modifications thereof, using readily available starting materials, reagents and conventional synthesis procedures. Unless otherwise specified, the various substituents of the compounds are defined in the same manner as they are defined above in Formula I in the "Summary of Invention" section.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In General Reaction Scheme No. 1, salicaldehyde or the corresponding mercapto compound (wherein $R^1$ is hydrogen or halogen) is reacted with base and to this is added a substituted 2-chloronitrobenzene (wherein $R_2$ is hydrogen or halogen). The resulting ether or thioether is reduced to yield substituted dibenz[b,f][1,4]oxazepine or sulfur analog, wherein $R^1$ and $R^2$ are as described hereinabove, wherein X is oxygen or sulfur. In the resulting compound $R^3$ is oxygen, —NH—, —N-alkyl, —N-aryl, —N-alkylenearyl or —N—, and can combine with $R^4$ and $R^8$ to form

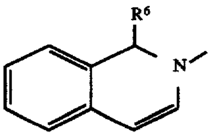

or

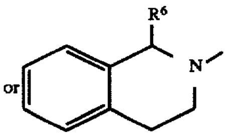

;

$R^4$ is carbon or —CH—, and can combine with $R^5$ to form carbonyl, a 4-, 5- or 6-membered non-aromatic, saturated, single-ring structure,

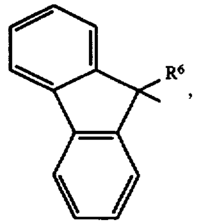

,

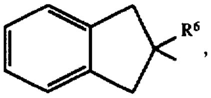

,

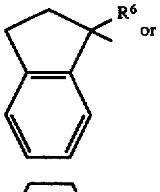

or

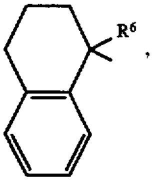

, and can combine with $R^3$ and $R^5$ to form

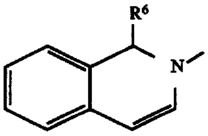

or

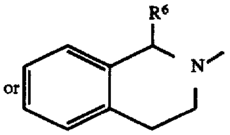

;

$R^5$ is $—(CH_2)_m—$, oxygen, aryl, aralkyl, arylcarbonylhydroxy, arylcarbonylalkoxy, a mono- or di-valent alkylenearyl or a mono- or divalent alkenylenearyl, and can combine with $R^4$ to form carbonyl, a 4-, 5- or 6-membered nonaromatic, saturated, single-ring structure,

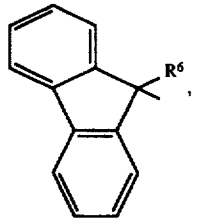

,

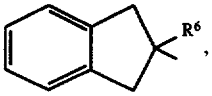

,

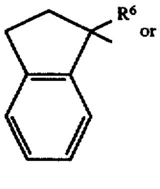

or

-continued

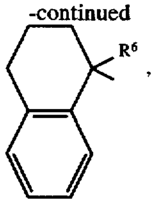

and can combine with $R^3$ and $R^4$ to form

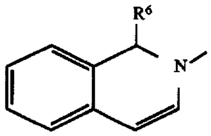
or
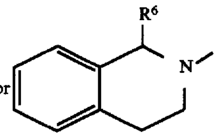
;

$R^6$ is a single covalent bond to the carbon 9 of said compound, or a single or double covalent bond to the carbon 11 of said compound; $R^7$ is hydrogen or halogen; p and q may be the same or different, and are 0 or 1; and m is 3, 4 or 5. $R^2$ cannot be at the carbon 9 position of the compound. Oxidation of the sulfur of the X variable is achieved with hydrogen peroxide to produce X as being

or
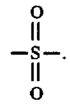

In General Reaction Scheme No. 2, a mixture of suitably protected substituted or unsubstituted dibenz[b,f][1,4]oxazepine or appropriate sulfur analog substituted with a carbamate in anhydrous solvent under an inert atmosphere is cooled, and is treated with a base to form an anion. The anion is then reacted with an electrophile, such as an aldehyde, and is worked up in the usual manner known by those of skill in the art to provide the products of the present invention. In General Reaction Scheme No. 2, X, $R^1$, $R^2$, $R^3$, $R^4$, $R^5$, $R^6$, $R^7$, p, q and m are as described above for General Reaction Scheme No. 1.

In General Reaction Scheme No. 3, a suitably protected dibenz[b,f][1,4]oxazepine or appropriate sulfur analog is treated with base and followed by an appropriate electrophile, the cyclization occurring in situ after the initial trap to give the corresponding products. In General Reaction Scheme No. 3, X, $R^1$, $R^2$, $R^3$, $R^4$, $R^5$, $R^6$, $R^7$, p, q and m are as described above for General Reaction Scheme No. 1.

GENERAL REACTION SCHEME NO. 1

A. For X = oxygen or sulfur

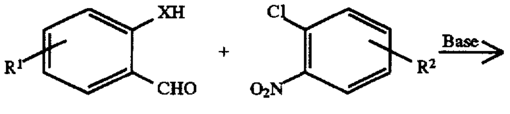

I II

-continued

GENERAL REACTION SCHEME NO. 1

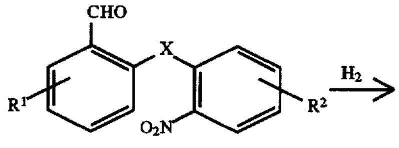

III

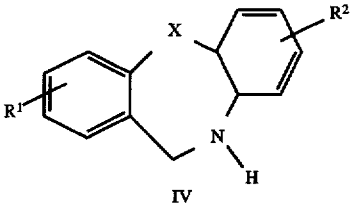

IV

B. For X = SO or $SO_2$:

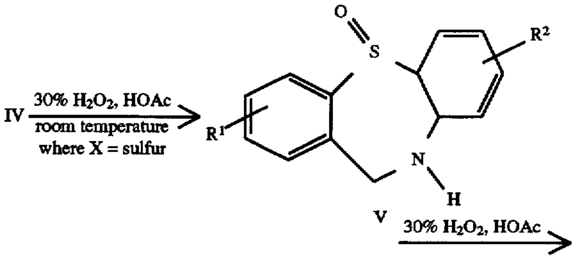

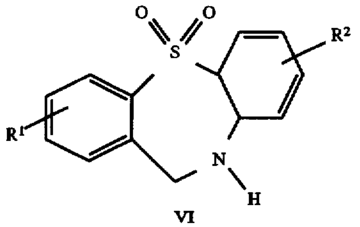

VI

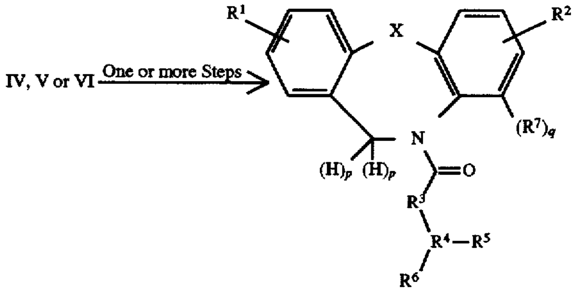

GENERAL REACTION SCHEME NO. 2

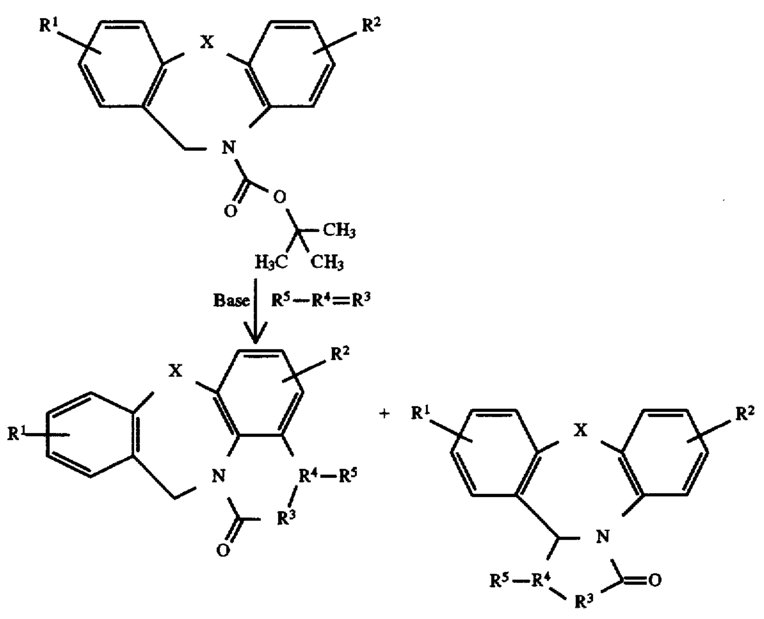

GENERAL REACTION SCHEME NO. 3

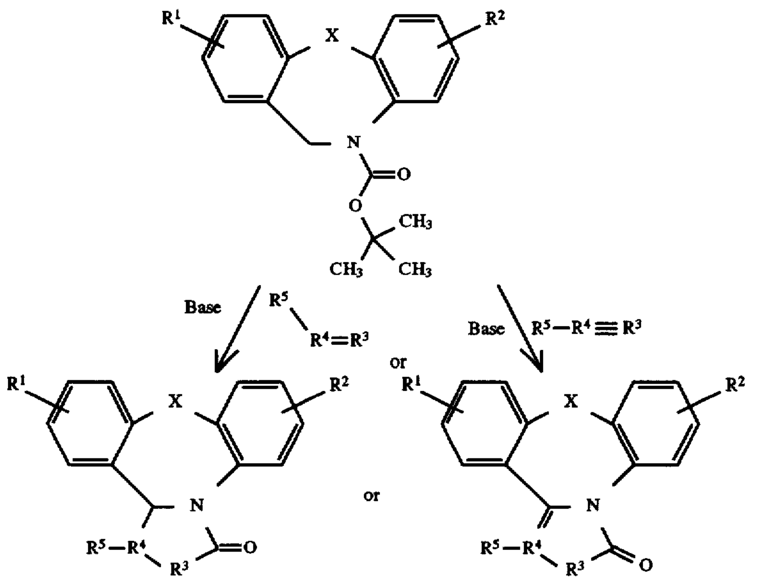

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the salt thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I as described above), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) EXAMPLES

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

Unless indicated otherwise in a particular example, all of the starting materials, and all of the equipment, employed in the examples are commercially available. Sources for these materials and equipment include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boshringer Mannheim Biochemicals (Indianapolis, Ind.), Fluka Chemical Corp. (Ronkonkoma, N.Y.), TCI, American Tokyo Kasei, Inc. (Atlanta, Ga.), Chemical Dynamics Corp. (South Plainfield, N.J.), Varian Associates, Inc. (Palo Alto, Calif.), VG Instruments, Inc. (Danvers, Mass.), Finnigan MAT (San Jose, Calif.), Millipore Corporation (Marlborough, Mass.) and Waters Associates. Most of the starting materials were obtained from Aldrich Chemical Co. (Milwaukee, Wis.). The syntheses of those starting materials which are not commercially available are described in the examples presented below.

Proton nuclear magnetic resonance spectra ($^1$H NMR, 300 MHz) were obtained on a Varian Unity 300, a VXR-300 or a XL-300 MHz NMR spectrometer. Chemical shifts (δ) are reported in parts per million down field from an internal tetramethylsilane or chloroform (7.24 ppm) reference. Deuterochloroform (99.8% D) was used as the solvent except where otherwise specified. When peak multiplicities are given, the following abbreviations are used: s, singlet; d, doublet; t, triplets q, quartet; m, multiplet; br, broadened; dt, doublet of triplet; dd, doublet of doublet; AB, AB quartet. Fast Atom Bombardment mass spectra (FABMS) were obtained on a VG40-250 mass spectrometer. Electron impact mass spectra (EIMS) were obtained on a Finnigan 4500 mass spectrometer. High-resolution mass spectra (HRMS) were obtained on a Finnigan MAT 90 mass spectrometer with FAB or EI ionization. High performance liquid chromatography (HPLC) separations were performed on a Waters Associates LC 2000 or Prep 500A System with silica gel columns. Melting points were determined on a Thomas-Hoover melting point apparatus, and are uncorrected. When involving air-sensitive reagents, all glassware was oven dried prior to use and all reactions were done under a nitrogen atmosphere. Elemental analyses were performed by Galbraith Laboratories, Inc. (Knoxville, Tenn.). Tetrahydrofuran (THF) was distilled from sodium and benzophenone under a nitrogen atmosphere. Lithium diisopropylamide (monotetrahydrofuran complex, 1.5M in cyclohexane) and methyllithium (1.4M in diethylether) were purchased from Aldrich Chemical Company. All other reagents and solvents were obtained from commercial sources and used without further purification.

All patents and publications referred to in the examples, and throughout the specification, are hereby incorporated herein by reference, without admission that such is prior art.

Example 1

1,1-dimethylethyl 8-chloro-dibenz[b,f][1,4]-oxazepine-10 (11H)-carboxylate (1)

Compound 1

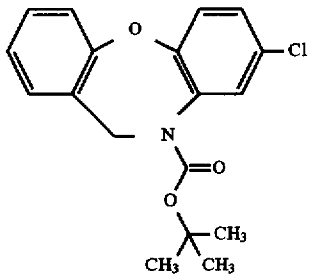

8-chloro-10,11-dihydrodibenz[b,f][1,4]oxazepine is synthesized in the manner described in U.S. Pat. No. 3,534,019, which is incorporated herein by reference.

Briefly, 200 parts of 2,5-dichloro-nitrobenzene were heated to 160° C. and stirred, and 160 parts of the potassium salt of salicaldehyde was added over a period of 30 minutes. After the addition was complete, an exothermic reaction took place, and the temperature rose to about 195° C. Heating was discontinued until the reaction subsided, and the mixture was heated for 1 hour at 150° C. The mixture was cooled, ice and water were added, and it was extracted with ether. The ether layer was filtered to remove insoluble material, and the resultant solution was dried over sodium sulfate. The ether solvent was evaporated, and the residual oil was recrystallized from a mixture of hexane and benzene to give 2-(2-nitro-4-chloro-phenoxy)benzaldehyde melting at about 100°-101° C.

A solution of 55 parts of the ether obtained in the preceding paragraph in 800 parts of ethanol was hydrogenated over Raney nickel catalyst at room temperature and atmospheric pressure. When hydrogen uptake ceased, the catalyst was removed by filtration, and the ethanol solvent was evaporated. The residue was dissolved in 500 parts by volume of hexane, filtered, and cooled. There was obtained yellowish-white crystals which were separated by filtration to give 8-chloro-10,11-dihydrodibenz[b,f][1,4]oxazepine melting at about 94°-95° C.

A solution of 8-chloro-10,11-dihydrodibenz[b,f][1,4]-oxazepine (15.0 g, 65 mmol), ditertbutyldicarbonate (17 g, 78 mmol) and DMAP (1 g, 8 mmol) in THF (500 mL) was refluxed under an $N_2$ atmosphere for 24 hours. The solvent was removed under reduced pressure to yield a yellow oil that was flash chromatographed on silica gel (10% EtOAc/hexane) to yield 20.5 g of 1 as a white solid (95.4%): mp 109°-110° C.

Analysis Calculated for $C_{18}H_{18}NO_3Cl$: C, 65.16; H, 5.47; N, 4.22. Found: C, 64.78; H, 5.51; N, 4.13.

Example 2

4-chloro-3-phenyl-1H,3H,12H-[3,1]-benzoxazino[8,1-b,c][1,4]benzoxazepin-1-one (2), 6-chloro-1,13b-dihydro-1-phenyl-3-dibenz[b,f]oxazolo[3,4d]-[1,4]oxazepin-3-one (3) and 6-chloro-1,13b-dihydro-1-phenyl-3H-dibenz[b,f]oxazolo-[3,4-d][1,4]oxazepin-3-one (4)

Compound 2

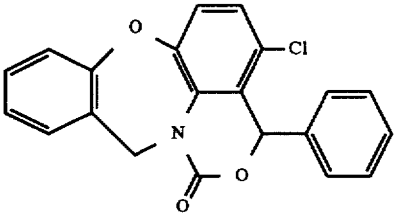

Compounds 3 and 4

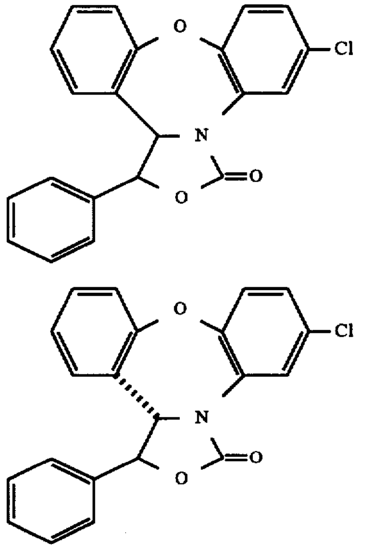

A stirring solution of 1 (2.0 g, 6.04 mmol) in 40 mL of THF was cooled to −78° C. followed by the addition of n-BuLi (1.6M, 4.32 mL, 6.91 mmol). The mixture was stirred at −78° C. for 30 minutes and treated with benzaldehyde (696 mg, 6.56 mmol), and then slowly warmed to room temperature and diluted with 16 mL of water. The mixture was then extracted with ether (200 mL×2), and the combined extracts were washed with brine (saturated, 50 mL) and dried ($Na_2SO_4$). The extracts were concentrated to give the crude product (3.04 g), which was purified by medium pressure chromatography with 10% EtOAc/hexane to a 100% EtOAc gradient elution, to yield 2, 3 and 4 as follows:

4-chloro-3-phenyl-1H,3H,12H-[3,1]-benzoxazino-[8,1-b,c][1,4]benzoxazepin-1-one 2 (420 mg) as a foam; Analysis Calculated for $C_{21}H_{14}NO_3Cl$: C, 69.33; H, 3.88; N, 3.85; Cl, 9.74. Found: C, 69.09; H, 4.25; N, 3.77; Cl, 9.59; and 6-chloro-1,13b-dihydro-1-phenyl-3H-dibenz[b,f]oxazolo-[3,4-d][1,4]oxazepin-3-one 3 (730 mg): DSC: 116.4° C.; Analysis Calculated for $C_{21}H_{14}NO_3Cl\times0.25\,H_2O$: C, 68.48; H, 3.97; N, 3.80; Cl, 9.63. Found: C, 68.31; H, 4.23; N, 3.95; Cl, 9.81; and 6-chloro-1,13b-dihydro-1-phenyl-3H-dibenz[b,f]oxazolo-[3,4-d][1,4]oxazepin-3-one 4 (780 mg): DSC: 213.07° C.; Analysis Calculated for $C_{21}H_{14}NO_3Cl\times0.25\,H_2O$: C, 68.48; H, 3.97; N, 3.80; Cl, 9.63. Found: C, 68.46; H, 3.90; N, 3.76; Cl, 9.57.

Example 3

4-chloro-3-(4-pyridyl)-1H,3H,12H-[3,1]-benzoxazino-[8,1-b,c][1,4]benzoxazepin-1-one (5), trans-6-chloro-1,13b-dihydro-1-(4-pyridyl)-3H-dibenz-[b,f]oxazolo[3,4-d][1,4]oxazepin-3-one (6) and cis-6-chloro-1,13b-dihydro-1-(4- pyridyl)-3H-dibenz[b,f]oxazolo-[3,4-d][1,4]oxazepin-3-one (7)

Compound 5

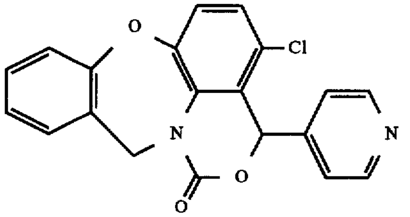

Compound 6

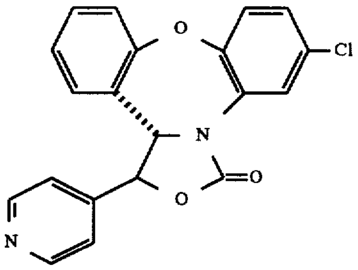

Compound 7

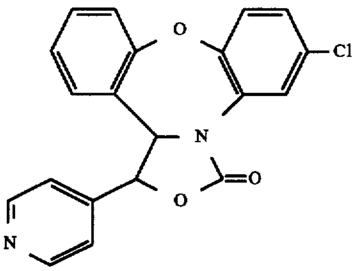

A stirring solution of 1 (2.0 g, 6.04 mmol) in 40 mL of THF was cooled to −78° C. followed by the addition of n-BuLi (1.6M, 4.32 mL, 6.91 mmol). The mixture was stirred at −78° C. for 30 minutes and treated with 4-pyridinecarboxalde (750 mg, 7 mmol), and then slowly warmed to room temperature and diluted with 16 mL of water. The mixture was then extracted with ether (200 mL×2), and the combined extracts were washed with brine (saturated, 200 mL) and dried ($Na_2SO_4$). The extracts were concentrated to give the crude product (3.0 g), which was purified by medium pressure chromatography with 5:95 MeoH:$CHCl_3$, to yield 5, 6 and 7 as follows:

4-chloro-3-(4-pyridyl)-1H,3H,12H-[3,1]-benzoxazino-[8, 1-b,c][1,4]-benzoxazepin-1-one 5 (300 mg) as a foam; Analysis Calculated for $C_{20}H_{13}N_2O_3Cl$×0.25 $H_2O$: C, 65.05; H, 3.69; N, 7.59; Cl, 9.60. Found: C, 65.18; H, 3.90; N, 7.20; Cl, 9.26;

trans-6-chloro-1,13b-dihydro-1-(4-pyridyl)-3H-dibenz[b, f]oxazolo[3,4-d][1,4]-oxazepin-3-one 6 (155 mg): DSC: 178.98° C.; Analysis Calculated for $C_{20}H_{13}N_2O_3Cl$: C, 65.85; H, 3.59; N, 7.68; Cl, 9.72. Found: C, 65.69; H, 3.74; N, 7.46; Cl, 9.78; and cis-6-chloro-1,13b-dihydro-1-(4-pyridyl)-3H-dibenz[b,f] -oxazolo[3,4-d][1,4]oxazepin-3-one 7 (576 mg): DSC: 216.87° C.; Analysis Calculated for $C_{20}H_{13}N_2O_3Cl$: C, 65.85; H, 3.59; N, 7.68; Cl, 9.72. Found: C, 65.55; H, 3.67; N, 7.58; Cl, 9.89.

(+)-4-chloro-3-(4-pyridyl)-1H,3H,12H-[3,1]benzoxazino-[8,1-b,c][1,4]benzoxazepin-1-one (5a) and (−)-4-chloro-3-(4-pyridyl)-1H,3H,12H-[3,1]-benzoxazino-[8,1-b,c][1,4] benzoxazepin-1-one (5a)

Compounds 5a and 5b

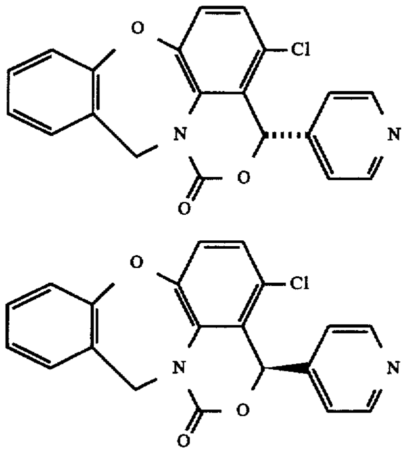

The enantiomers of 4-chloro-3-(4-pyridyl)-1H,3H,12H-[3,1]-benzoxazino[8,1-b,c][1,4]benzoxazepin-1-one 5 can be seperated by HPLC on a chiral column to yield (+)-4-chloro-3-(4-pyridyl)-1H,3H,12H-[3,1]-benzoxazino-[8,1-b, c][1, 4]benzoxazepin-1-one 5a (specific rotation +186.5° at 589 nM, mp: 84°–85° C.) and (−)-4-chloro-3-(4-pyridyl)-1H,3H,12H-[3,1]-benzoxazino[8,1-b,c][1, 4]benzoxazepin-1-one 5b (specific rotation −157.1° at 589 nM, mp: 84°–85° C.).

(+)-trans-6-chloro-1,13b-dihydro-1-(4-pyridyl-3H-dibenz [b,f]oxazolo[3,4-d][1,4]oxazepin-3-one (6a) and (−)-trans-6-chloro-1,13b-dihydro-1-(4-pyridyl)-3H-dibenz[b,f] oxazolo-[3,4-d][1,4]oxazepin-3-one (6b)

Compounds 6a and 6b

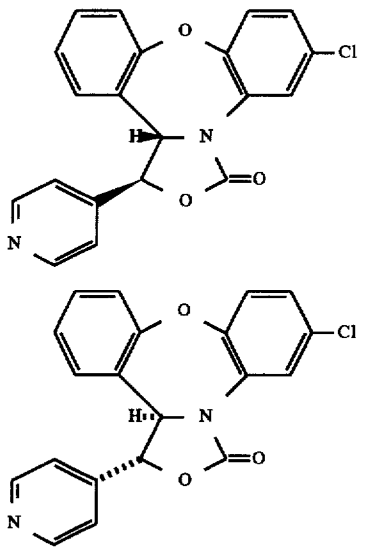

The enantiomers of trans-6-chloro-1,13b-dihydro-1-(4-pyridyl)-3H-dibenz[b,f]oxazolo[3,4-d][1,4]-oxazepin-3-one 6 can be separated by HPLC on a chiral column to yield 6a and 6b as follows:

(+)-trans-6-chloro-1,13b-dihydro-1-(4-pyridyl)-3H-dibenz[b,f]oxazolo[3,4-d][1,4]oxazepin-3-one 6a specific rotation +67.7° @ 589 nM; Analysis Calculated for $C_{20}H_{13}N_2O_3Cl$×1 $H_2O$: C, 62.75; H, 3.95; N, 7.32. Found: C, 63.06; H, 4.11; N, 6.95; and (−)-trans-6-chloro-1,13b-dihydro-1-(4-pyridyl)-3H-dibenz[b,f]oxazolo[3,4-d][1,4]oxazepin-3-one 6b specific rotation −50.2° @ 589 nM; Analysis Calculated for $C_{20}H_{13}N_2O_3Cl \times 1.5\ H_2O$: C, 61.31; H, 4.12; N, 7.15. Found: C, 61.38; H, 4.13; N, 6.82.

Example 4

4-chloro-3-(3-pyridyl)-1H,3H,12H-[3,1]-benzoxazino-[8,1-b,c][1,4]benzoxazepin-1-one (8), 6-chloro-1,13b-dihydro-1-(3-pyridyl)-3H-dibenz[b,f]oxazolo-[3,4-d][1,4]-oxazepin-3-one (9a) and 6chloro-1,13b-dihydro-1-(3-pyridyl)-3H-dibenz[b,f]-oxazolo-[3,4-d][1,4]oxazepin-3-one (9b)

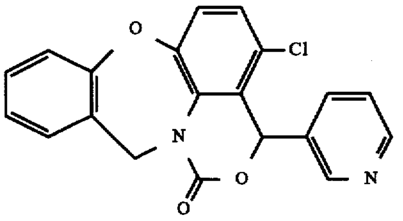

Compound 8

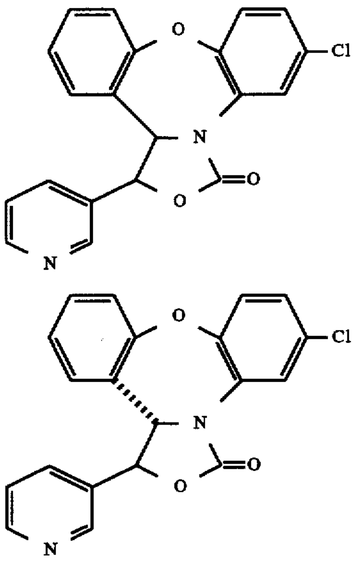

Compounds 9a and 9b

A stirring solution of 1 (1.0 g, 3.01 mmol) in 20 mL of THF was cooled to −78° C. followed by the addition of n-BuLi (1.6M, 2.2 mL, 3.5 mmol). The mixture was stirred at −78° C. for 30 minutes and treated with 3-pyridinecarboxalde (0.33 mL, 3.5 mmol) then slowly warmed to room temperature. EtOAc (150 mL) and brine (saturated, 50 mL) was then added to the reaction mixture, and the layers were separated and the organic solution was dried ($Na_2SO_4$). The organic solution was concentrated to give the crude product (1.1 g), which was purified by medium pressure chromatography with 5:40:55 MeoH:EtOAc:Hexane, to yield 8, 9a and 9b as follows:

4-chloro-3-(3-pyridyl)-1H,3H,12H-[3,1]-benzoxazino-[8,1-b,c][1,4]benzoxazepin-1-one 8 (184 mg) as a foam; Analysis Calculated for $C_{20}H_{13}N_2O_3Cl \times 0.05\ CHCl_3$: C, 64.95; H, 3.55; N, 7.56; Cl, 11.00. Found: C, 64.81; H, 3.62; N, 7.51; Cl, 10.97; and 6-chloro-1,13b-dihydro-1-(3-pyridyl)-3H-dibenz[b,f]-oxazolo[3,4-d][1,4]oxazepin-3-one 9a; and 6-chloro-1,13b-dihydro-1-(3-pyridyl)-3H-dibenz[b,f]-oxazolo[3,4-d][1,4]oxazepin-3-one 9b (246 mg): DSC: 220.87° C.; Analysis Calculated for $C_{20}H_{13}N_2O_3Cl$: C, 65.85; H, 3.59; N, 7.68; Cl, 9.72. Found: C, 65.43; H, 3.69; N, 7.61; Cl, 9.92.

Example 5

6-chloro-1,13b-dihydro-1-(2-pyridyl)-3H-dibenz-[b,f]oxazolo[3,4-d][1,4]oxazepin-3-one (10) and cis-6-chloro-1,13b-dihydro-1-(2-pyridyl)-3H-dibenz[b,f]oxazolo[3,4-d][1,4]-oxazepin-3-one (11)

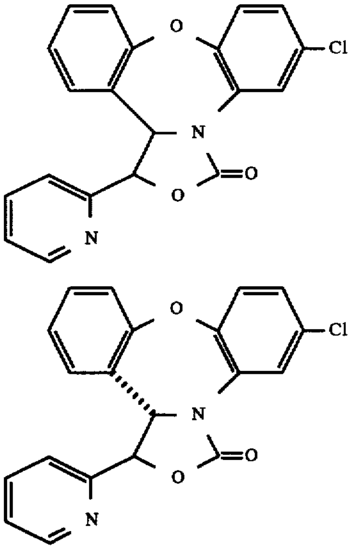

Compounds 10 and 11

A stirring solution of 1 (2.0 g, 6.04 mmol) in 40 mL of THF was cooled to −78° C., followed by the addition of n-BuLi (1.6M, 4.32 mL, 6.91 mmol). The mixture was stirred at −78° C. for 30 minutes and treated with 2-pyridinecarboxalde (750 mg, 7 mmol), and then slowly warmed to room temperature and let stir for 1.5 hours at room temperature, and then diluted with 16 mL of water. The mixture was then extracted with ethyl acetate (200 mL×2), and the combined extracts were washed with brine (saturated, 200 mL) and dried ($Na_2SO_4$). The extracts were concentrated to give the crude product (2.6 g), which was purified by medium pressure chromatography with 5:95 MeoH:$CHCl_3$, to yield 10 and 11 as follows:

6-chloro-1,13b-dihydro-1-(2-pyridyl)-3H-dibenz[b,f]-oxazolo[3,4-d][1,4]oxazepin-3-one 10 (671 mg): DSC: 151.42° C.; Analysis Calculated for $C_{20}H_{13}O_3Cl$: C, 65.85; H, 3.59; N, 7.68; Cl, 9.72. Found: C, 65.87; H, 3.61; N, 7.59; Cl, 9.68; and 6-chloro-1,13b-dihydro-1-(2-pyridyl)-3H-dibenz[b,f]-oxazolo[3,4-d][1,4]oxazepin-3-one 11 (188 mg): DSC: 220.87° C.; Analysis Calculated for $C_{20}H_{13}N_2O_3Cl$: C, 65.85; H, 3.59; N, 7.68; Cl, 9.72. Found: C, 65.61; H, 3.48; N, 7.52; Cl, 9.96.

Example 6

6-chloro-1,13b-dihydro-1-(3-thienyl)-3H-dibenz[b,f]oxazolo[3,4-d][1,4]-oxazepin-3-one (12)

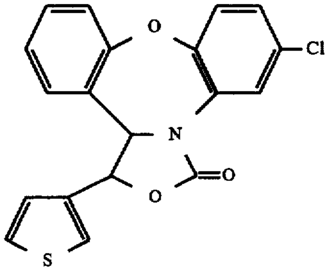

Compound 12

A stirring solution of 1 (2.0 g, 6.04 mmol) in 40 mL of THF was cooled to −78° C. followed by the addition of n-BuLi (1.6M, 4.32 mL, 6.91 mmol). The mixture was stirred at −78° C. for 30 minutes and treated with 3-thiophenecarboxalde (750 mg, 7 mmol), and then slowly warmed to room temperature and let stir for 1.5 hours at room temperature, and then diluted with 16 mL of water. The mixture was then extracted with ethyl acetate (200 mL×2) and the combined extracts were washed with brine (saturated, 200 mL) and dried ($Na_2SO_4$). The extracts were concentrated to give the crude product (2.52 g), which was purified by medium pressure chromatography with 10:90 EtOAc:Hexane to yield 6-chloro-1,13b-dihydro-1-(3-thienyl)-3H-dibenz[b,f]oxazolo[3,4-d][1,4]oxazepin-3-one 12 (429 mg): DSC: 182.5° C.; Analysis Calculated for $C_{29}H_{12}NO_3SCl$×0.1 $H_2O$: C, 61.41; H, 3.31; N, 3.77; S, 8.63; Cl, 9.54. Found: C, 61.25; H, 3.30; N, 3.66; S, 8.69; Cl, 9.71.

Example 7

4-chloro-3-(-2-furyl)-1H,3H,12H-[3,1-benzoxazino-[8,1-b,c][1,4]-benzoxazepin-1-one (13), 6-chloro-1,13b-dihydro-1-(-2-furyl)-3H-dibenz[b,f]-oxazolo-[3,4-d][1,4]oxazepin-3-one (14a) and 6-chloro-1,13b-dihydro-1-(-2-furyl)-3H-dibenz[b,f]-oxazolo[3,4-d][1,4]-oxazepin-3-one (14b)

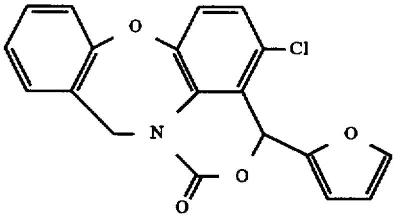

Compound 13

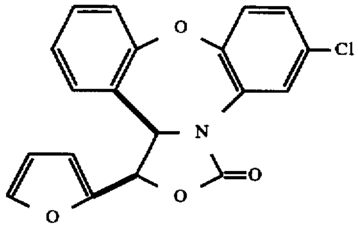

Compounds 14a and

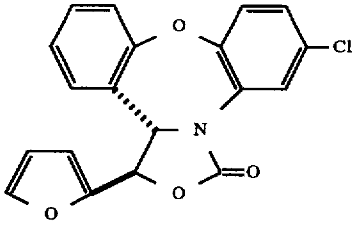

14b

A stirring solution of 1 (2.0 g, 6.04 mmol) in 40 mL of THF was cooled to −78° C. followed by the addition of n-BuLi (1.6M, 4.32 mL, 6.91 mmol). The mixture was stirred at −78° C. for 30 minutes and treated with furalaldehyde (670 mg, 6.97 mmol) and then slowly warmed to room temperature and diluted with 16 mL of water. The mixture was then extracted with ether (200 mL×2) and the combined extracts were washed with brine (saturated, 50 mL) and dried ($Na_2SO_4$). The extracts were concentrated to give the crude product (2.5 g), which was purified by HPLC with 20% EtOAc/heptane to yield Compounds 13, 14a and 14b as follows:

4-chloro-3-(-2-furyl)-1H,3H,12H-[3,1]-benzoxazino-[8,1-b,c][1,4]benzoxazepin-1-one (13) (320 mg): mp 168°–170° C.; Analysis Calculated for $C_{19}H_{12}NO_3Cl$× $H_2O$: C, 64.14; H, 3.97; N, 3.94; Cl, 9.96. Found: C, 64.07; H, 3.99; N, 3.88; Cl, 10.26.

The cis and trans isomers (Compounds 14a and 14b) were not separated under these conditions, and gave one fraction (310 mg): m.p. 170.5°–173.5° C.; Analysis Calculated for $C_{19}H_{12}NO_3Cl$×1.1 $H_2O$: C, 63.82; H, 4.00, N, 3.92; Cl, 9.91. Found: C, 63.79; H, 3.62; N, 3.79; Cl, 9.85.

Example 8

6-chloro-1,13b-dihydro-1-(-N-methylpyrryl)-3H-dibenz[b,f]-oxazolo-[3,4-d][1,4]oxazepin-3-one (15a) and 6-chloro-1,13b-dihydro-1-(-N-methylpyrryl-3H-dibenz[b,f]-oxazolo [3,4-d][1,4]-oxazepin-3-one (15b)

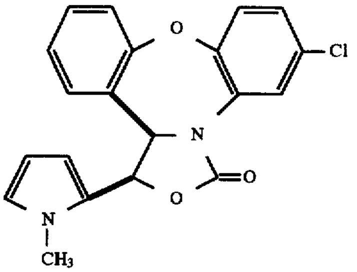

Compounds 15a and

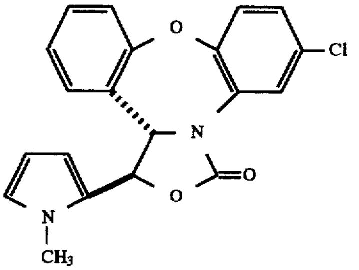

15b

A stirring solution of 1 (2.0 g, 6.04 mmol) in 40 mL of THF was cooled to −78° C. followed by the addition of n-BuLi (1.6M, 4.32 mL, 6.91 mmol). The mixture was stirred at −78° C. for 30 minutes and treated with N-methylpyrrol-2-carboxyaldehyde (764 mg, 7.00 mmol), then slowly warmed to room temperature and diluted with 16 mL of water. The mixture was extracted with ether (200 mL×2) and the combined extracts were washed with brine (saturated, 50 mL) and dried ($Na_2SO_4$). The extracts were concentrated to give the crude product which was purified by HPLC using 20% EtOAc/heptane to yield 15a and 15b in one fraction (the cis and trans isomers not being separated) (280mg): mp 149°–152° C.; Analysis Calculated for $C_{21}H_{17}N_2O_3Cl$×0.25 H2O: C,65.46; H, 4.58; N, 7.27; Cl, 9.20. Found: C, 65.18; H, 4.95; N, 7.05; Cl, 9.12.

Example 9

6-chloro-1,13b-dihydro-1-(-4-carboxymethlyphenyl)-3H-dibenz[b,f]-oxazolo-[3,4-d][1,4]oxazepin-3-one (16) and 6-chloro-1,13b-dihydro-1-(4-carboxymethylphenyl)-3H-dibenz[b,f]-oxazolo[3,4-d][1,4]-oxazepin-3-one (17)

Compounds 16

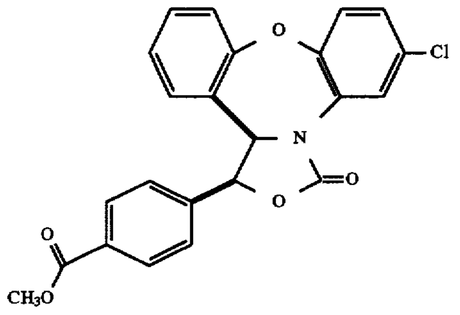

and

17

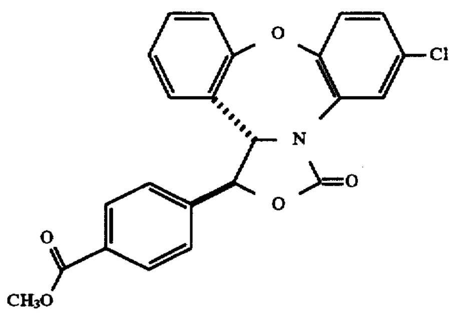

A stirring solution of 1 (2.0 g, 6.04 mmol) in 40 mL of THF was cooled to −78° C. followed by the addition of n-BuLi (1.6M, 4.32 mL, 6.91 mmol). The mixture was stirred at −78° C. for 30 minutes and treated with methyl 4-formyl benzoate (1.2 g, 7 mmol), and then slowly warmed to room temperature and let stir for 1.5 hours at room temperature, and then diluted with 16 mL of water. The mixture was then extracted with ethyl acetate (200 mL×2) and the combined extracts were washed with brine (saturated, 200 mL) and dried ($Na_2SO_4$). The extracts were concentrated to give the crude product (2.95g), which was purified by medium pressure chromatography with 1:4 EtOAc:Hexane, to yield 16 and 17 as follows:

6-chloro-1,13b-dihydro-1-(4-carboxymethyl)-3H-dibenz[b,f]oxazolo[3,4-d][1,4]oxazepin-3-one 16 (320 mg): DSC: 217.88° C.; Analysis Calculated for $C_{23}H_{16}NO_5Cl$×0.25 $H_2O$: C, 64.79; H, 3.90; N, 3.29; Cl, 8.32. Found: C, 64.85; H, 3.65; N, 3.30; Cl, 8.41; and 6-chloro-1,13b-dihydro-1-(4-arboxymethylphenyl)-3H-dibenz[b,f]oxazolo-[3,4-d][1,4]oxazepin-3-one 17 (1.26 g): DSC: 233.9° C.; Analysis Calculated for $C_{23}H_{16}NO_5Cl$: C, 65.45; H, 3.82; N, 3.32; Cl, 8.40. Found: C, 65.10; H, 3.72; N, 3.28 Cl, 8.39.

Example 10

6-chloro-1,13b-dihydro-1-(-4-carboxylic acid phenyl)-3H-dibenz[b,f]-oxazolo-[3,4-d][1,4]-oxazepin-3-one (18)

Compound 18

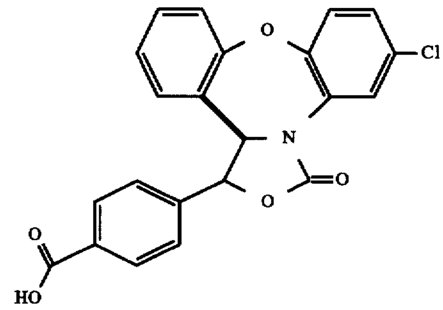

To a stirring solution of 17 (77 mg, 0.18 mmol) in THF (3 mL) and MeOH (1.5 mL) was added NaOH (0.55 mL, 1M, 0.55 mmol). The resulting solution was stirred for 2.5 hours, followed by the removal of solvent under reduced pressure. To the residue was added 0.6 mL of 1M HCl. The resulting precipitate was collected by filtration and dried to yield 18 (57 mg): DSC: 217.88° C.; Analysis Calculated for $C_{22}H_{14}NO_5Cl$×3.5 $H_2O$: C, 56.24; H, 4.29; N, 2.98. Found: C, 55.84; H, 3.90; N, 2.91.

Example 11

6-chloro-1,13b-dihydro-1-(phenyl)-3-(methyl)-dibenz[b,f]-imidazolo[3,4-d][1,4]-oxazepin-3-one (19)

Compound 19

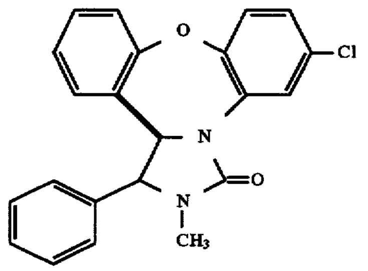

A stirring solution of 1 (2.0 g, 6.04 mmol) in 40 mL of THF was cooled to −78° C., followed by the addition of n-BuLi (1.6M, 4.32 mL, 6.91 mmol). The mixture was stirred at −78° C. for 30 minutes, treated with N-bezylidinemethyl-amine (834 mg, 7 mmol), and then slowly warmed to room temperature and then diluted with 16 mL of water. The mixture was then extracted with ethyl acetate (200 mL×2), and the combined extracts were washed with brine (saturated, 200 mL) and dried ($Na_2SO_4$). The extracts were concentrated to give the crude product (2.72 g), which was purified by medium pressure chromatography with 1:1 EtOAc:Hexane, to yield 6-chloro-1,13b-dihydro-1-(phenyl)-3-(methyl)-dibenz[b,f]imidazolo[3,4-d][1,4]oxazepin-3-one 19 (725 mg): DSC: 102.45° C.; Analysis Calculated for $C_{22}H_{17}N_2O_2Cl$×0.33 $CHCl_3$×0.1 $H_2O$: C, 63.74; H, 4.27; N, 6.66; Cl, 16.77. Found: C, 63.95; H, 4.30; N, 6.46; Cl, 16.43.

Example 12

6-Chloro-1,13b-dihydro-1-[2,4,6-trimethyl]phenyl-3H-dibenz[b,f]oxazolo[3,4-d][1,4]oxazepin-3-one (20a) and 6-chloro-1,13b-dihydro-1-[2,4,6-trimethyl]-phenyl-3H-dibenz[b,f]oxazolo[3,4-d][1,4]-oxazepin-3-one (20b)

Compounds 20a

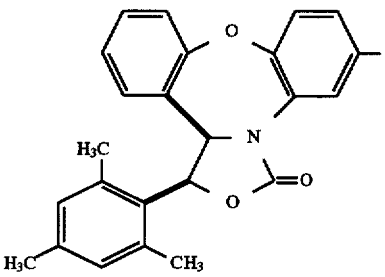

and

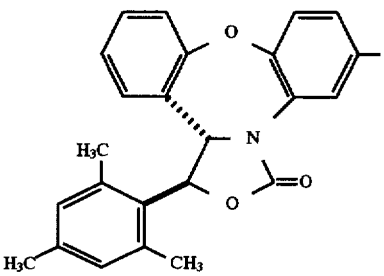

20b

A stirring solution of 1 (2.0 g, 6.04 mmol) in 40 mL of THF was cooled to −78° C. followed by the addition of n-BuLi (1.6M, 4.32 mL, 6.91 mmol). The mixture was stirred at −78° C. for 30 minutes and treated with mesitaldehyde (1.04 g, 7.0 mmol), and then slowly warmed to room temperature and diluted with 16 mL of water. The mixture was then extracted with ether (200 mL×2) and the combined extracts were washed with brine (saturated, 50 mL) and dried ($Na_2SO_4$). The extracts were concentrated to give the crude product (3.04 g), which was purified by medium pressure chromatography with 20% EtOAc/heptane, to yield 20a and 20b as a 3:2 mixture after recrystallization from EtOAC/hexane. DSC: 169.95° C. Analysis Calculated for $C_{24}H_{20}NO_3Cl$: C, 71.02; H, 4.97; N, 3.45; Cl, 8.73. Found: C, 71.34; H, 5.29; N, 3.40; Cl, 9.12.

Example 13

6-Chloro-1,13b-dihydro-3H-spiro[dibenz[b,f]oxazolo-[3,4-d][1,4]oxazepin-1,1'-cyclobutan]-3-one (21)

Compound 21

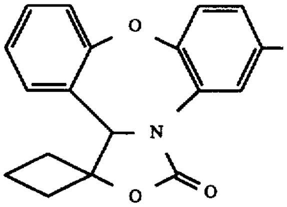

To a stirred solution of 1.0 g (3.0 mmol) of 1 in 20 mL of anhydrous THF was added 1.2 equivalent of lithium diisopropylamide at −78°. After 30 minutes, approximately 2 equivalent of cyclobutanone was added as the electrophile. The stirring was continued for 3 hours at −78°, followed by room temperature overnight, and was quenched with saturated ammonium chloride solution. The mixture was diluted with ethyl acetate, washed with brine and dried with magnesium sulfate or sodium sulfate. Purification by HPLC on silica gel with 7% ethyl acetate/hexane as the eluent followed by lyophilization from acetonitrile/water gave 355 mg (36%) of Compound 21. $^1$H NMR ($CDCl_3$): δ 7.62 (s, 1H, ArH), 7.16–7.40 (m, 6H, ArH), 5.19 (s, 1H, ArCH), 2.75–2.84 (m, 1H, c-butyl), 2.45–2.60 (m, 1H, c-butyl), 2.28–2.42 (m, 1H, c-butyl), 2.12–2.26 (m, 1H, c-butyl), 1.82–2.00 (m, 1H, c-butyl), 1.30–1.45 (m, 1H, c-butyl). FABMS: m/z 334 (M+Li). HRMS calculated for $C_{18}H_{14}NO_3LiCl$ (M+Li) 334.0822, found 334.0867. Analysis Calculated for $C_{18}H_{14}NO_3Cl$: C, 65.96; H, 4.31; N, 4.27; Cl, 10.82. Found: C, 65.86; H, 4.31; N, 4.31; Cl, 10.46.

Example 14

6-chloro-1,13H-spiro[dibenz[b,f]-oxazolo3,4-d][1,4]oxazepin-1,1'-cyclopentane-3-one (22)

Compound 22

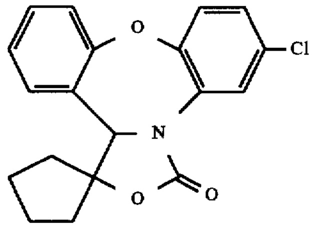

Compound 22 was prepared following the general methodology described in Example 13, except that cyclopentanone was employed as the electrophile. Silica gel purification with 5% ethyl acetate/hexane followed by lyophilization from acetonitrile/water gave 443 mg (43%) of Compound 22. $^1$H NMR ($CDCl_3$): δ 7.62 (S, 1H, ArH), 7.31 (d, J=4 Hz, 2H, ArH), 7.06–7.20 (m, 4H, ArH), 5.21 (s, 1H, ArCH), 2.26–2.38 (m, 1H, c-pentyl), 1.98–2.14 (m, 1H, c-pentyl), 1.72–1.95 (m, 3H, c-pentyl), 1.60–1.72 (m, 1H, c-pentyl), 1.39–1.55 (m, 1H, c-pentyl), 1.25–1.38 (m, 1H, c-pentyl). FABMS: m/z 348 (M+Li). HRMS calculated for $C_{19}H_{16}NO_3LiCl$ (M+Li) 348.0979, Found 348.0997. Analysis Calculated for $C_{19}H_{16}NO_3Cl$: C, 66.77; H, 4.72; N, 4.10; Cl, 10.37. Found: C, 66.54; H, 4.82; N, 4.05; Cl, 10.12.

Example 15

6-Chloro-1,13b-dihydro-3H-spiro[dibenz[b,f]oxazolo-[3,4-d][1,4]oxazepin-1,1'-cyclohexan]-3-one (23)

Compound 23

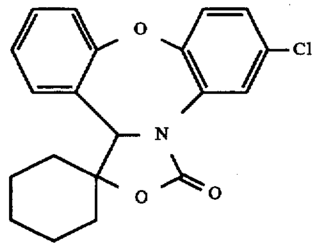

Compound 23 was prepared following the general methodology described in Example 13, except that cyclohexanone was employed as the electrophile. Silica gel purification with 10% ethyl acetate/hexane followed by lyophilization from acetonitrile/water gave 419 mg (39%) of Compound 23. $^1$H NMR ($CDCl_3$): δ 7.60 (s, 1H, ArH), 7.31 (s, 2H, ArH), 7.02–7.21 (m, 4H, ArH), 4.90 (s, 1H, ArCH), 2.10–2.18 (m, 1H, c-hexyl), 1.94–2.05 (m, 1H, c-hexyl), 1.60–1.93 (m, 5H, c-hexyl), 1.42–1.57 (m, 1H, c-hexyl), 1.00–1.18 (m, 1H, c-hexyl), 0.72–0.86 (m, 1H, c-hexyl). FABMS: m/z 362 (M+Li). HRMS calculated for $C_{20}H_{18}NO_3LiCl$ (M+Li) 362.1135, found 362.1143. Analysis Calculated for $C_{20}H_{18}NO_3Cl$: C, 67.51; H, 5.10; N, 3.94; Cl, 9.96. Found: C, 66.52; H, 5.19; N, 3.89; Cl, 9.57.

Example 16

6-Chloro-1,13b-dihydro-3H,9'H-spiro[dibenz[b,f]oxazolo-[3,4-d][1,4]oxazepin-1,9'-fluoren]-3-one (24)

Compound 24

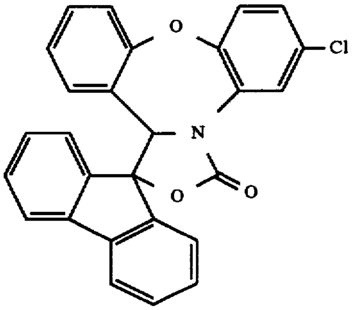

Compound 24 was prepared following the general methodology described in Example 13, except that 9-fluorenone was employed as the electrophile. Silica gel purification with 5% ethyl acetate/hexane followed by lyophilization from acetonitrile/water gave 231 mg (18%) of Compound 24. $^1$H NMR ($CDCl_3$): δ 7.73–7.77 (m, 2H, ArH), 7.66 (d, J=7 Hz, 1H, ArH), 7.56 (d, J=7 Hz, 1H, ArH), 7.35–7.49 (m, 4H, ArH), 7.12–7.25 (m, 2H, ArCH), 6.99–7.04 (m, 2H, ArH), 6.92 (t, J=7 Hz, 1H, ArH), 6.51 (d, J=8 Hz, 1H, ArH), 6.04 (d, J=7 Hz, 1H, ArH), 5.71 (s, 1H, ArCH). FABMS: m/z 438 (M+H). HEMS calculated for $C_{27}H_{16}NO_3LiCl$ (M+Li) 444.0979, found 444.1004. Analysis Calculated for $C_{27}H_{16}NO_3Cl$: C, 74.06; H, 3.68; N, 3.20; Cl, 8.10. Found: C, 73.82; H, 3.75; N, 3.28; Cl, 8.16.

Example 17

6-Chloro-1,13b-dihydro-3H-spiro[dibenz[b,f]oxazolo-[3,4-d[1,2'-oxazepin-1,2'-indan]-3-one (25)

Compound 25

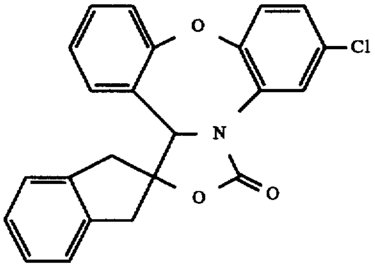

Compound 25 was prepared following the general methodology described in Example 13, except that 2-indanone was employed as the electrophile. Silica gel purification with 10% ethyl acetate/hexane followed by lyophilization from acetonitrile/water gave 133 mg (11%) of Compound 25. $^1$H NMR ($CDCl_3$): δ 7.58 (s, 1H, ArH), 7.00–7.29 (m, 7H, ArH), 6.80–6.95 (m, 3H, ArH), 5.28 (S, 1H, ArCH), 3.53 (AB, $J_{AB}$=18 Hz, ΔV=38 Hz, 2H, $ArCH_2$), 3.00 (AB, $J_{AB}$=18 Hz, ΔV=57 HZ, 2H, $ArCH_2$). FABMS: m/z 396 (M+Li). HRMS calculated for $C_{23}H_{16}NO_3LiCl$ (M+Li) 396.0979, found 396.1015. Analysis Calculated for $C_{23}H_{16}NO_3Cl$: C, 70.86; H, 4.14; N, 3.59; Cl, 9.09. Found: C, 70.76; H, 4.13; N, 3.67; Cl, 9.50.

Example 18

6-Chloro-1,13b-dihydro-3H-spiro[dibenz[b,f]oxazolo-[3,4-d][1,4]oxazepin-1,1'-indan]-3-one (26a) and 6-Chloro-1,13b-dihydro-3H-spiro[dibenz[b,f]-oxazolo[3,4-d][1,4]oxazepin-1,1'-indan]-3-one (26b)

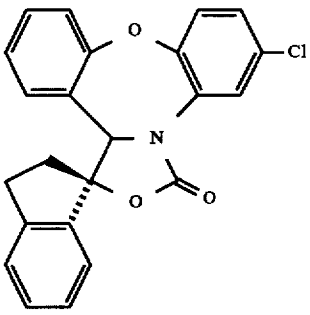

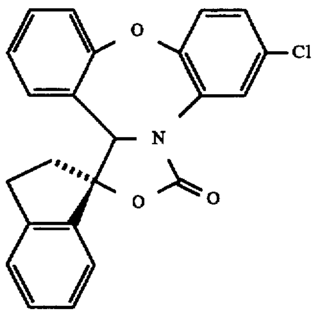

Compounds 26a and 26b

Compounds 26a and 26b were prepared following the general methodology described in Example 13, except that 1-indanone was employed as the electrophile. Silica gel purification with 10% ethyl acetate/hexane as the eluent gave two diastereoisomers (Compounds 26a and 26b). Both of the diastereoisomers were lyophilized from acetonitrile/water, and this gave 85 mg (7%) of higher Rf isomer and 365 mg (31%) of lower Rf isomer.

For isomer with higher Rf: $^1$H NMR ($CDCl_3$): δ 7.67 (s, 1H, ArH), 7.58–7.61 (m, 1H, ArH), 7.32–7.38 (m, 2H, ArH), 7.13–7.26 (m, 5H, ArH), 6.76 (t, J=7 Hz, 1H, ArH), 6.15 (t, J=7 Hz, 1H, ArH), 5.31 (s, 1H, ArCH), 2.72–2.81 (m, 1H), 2.41–2.50 (m, 1H), 2.15–2.23 (m, 1H), 1.87–1.98 (m, 1H). FABMS: m/z 396 (M+Li). HRMS calculated for $C_{23}H_{16}NO_3LiCl$ (M+Li) 396.0979, found 396.0933. Analysis Calculated for $C_{23}H_6NO_3Cl$: C, 70.86; H, 4.14; N, 3.59; Cl, 9.09. Found: C, 70.92; H, 4.12; N, 3.55; Cl, 10.17.

For isomer with lower Rf: $^1$H NMR ($CDCl_3$): δ 7.62 (s, 1H, ArH), 7.41 (d, J=8 Hz, 1H, ArH), 6.92–7.18 (m, 7H, ArH), 6.77–6.79 (m, 2H, ArH), 5.43 (s, 1H, ArCH), 3.03–3.13 (m, 1H), 2.63–2.90 (m, 3H). FABMS: m/z 396 (M+Li). HRMS calculated for $C_{23}H_{16}NO_3LiCl$ (M+Li) 396.0979, found 396.1025. Analysis Calculated for $C_{23}H_{16}NO_3Cl$: C, 70.86; H, 4.14; N, 3.59; Cl, 9.09. Found: C, 70.51; H, 4.29; N, 3.49; Cl, 9.36.

Example 19

6-Chloro-1,1',2',3',4'-13b-hexahydro-3H-spiro[dibenz-[b,f]oxazolo[3,4-d [1,4]oxazepin-11'-naphthalen-]3-one (27a) and 6-Chloro-1,1'2',3',4'-13b-hexahydro-3H-spiro[dibenz[b,f]oxazolo[3,4-d][1,4]oxazepin-1,1'-naphthalen]-3-one (27b)

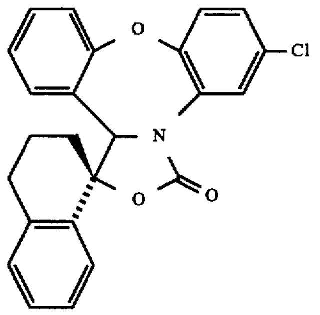

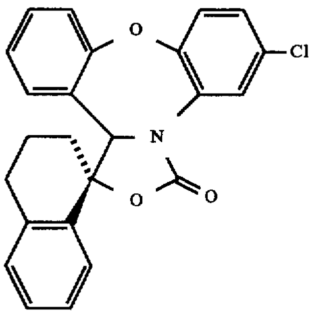

Compounds 27a and 27b

Compounds 27a and 27b were prepared following the general methodology described in Example 13, except that α-tetralone was employed as the electrophile. Silica gel purification with 10% ethyl acetate/hexane as the eluent gave two diastereoisomers (Compounds 27a and 27b). Both of the diastereoisomers were lyophilized from acetonitrile/water, and this gave 311 mg (26%) of higher Rf isomer and 94 mg (8%) of lower Rf isomer.

For isomer with higher Rf: $^1$H NMR ($CDCl_3$): δ 7.69–7.73 (m, 2H, ArH), 7.07–7.34 (m, 6H, ArH), 6.18 (t, J=7 Hz, 1H, ArH), 6.29 (t, J=8 Hz, 1H, ArH), 5.59 (s, 1H, ArCH), 2.62–2.71 (m, 1H), 2.39–2.49 (m, 1H), 1.91–2.12 (m, 2H), 1.61–1.69 (m, 1H), 1.02–1.14 (m, 1H). FABMS: m/z 410 (M+Li). HRMS calculated for $C_{24}H_{18}NO_3LiCl$ (M+Li) 410.1135, found 410.1111. Analysis Calculated for $CH_{24}H_{18}NO_3Cl$: C, 71.38; H, 4.49; N, 3.47; Cl, 8.78. Found: C, 71.47; H, 4.56; N, 3.56; Cl, 8.92.

For isomer with lower Rf. $^1$H NMR ($CDCl_3$): δ 7.59 (s, 1H, ArH), 7.18–7.28 (m, 3H, ArH), 7.15 (d, J=6 Hz, 1H, ArH), 6.94–7.06 (m, 3H, ArH), 6.84 (t, J=7 Hz, 1H, ArH), 6.68 (t, J=7 Hz, 1H, ArH), 6.56 (t, J=6 Hz, 1H, ArH), 5.26 (s, 1H, ArCH), 2.68–2.96 (m, 2H), 2.46–2.58 (m, 2H), 2.00–2.20 (m, 2H). FABMS: m/z 410 (M+Li). HRMS calculated for $C_{24}H_{18}NO_3LiCl$ (M+Li) 410.1135, found 410.1136. Analysis Calculated for $C_{24}H_{18}NO_3Cl$ (0.31 $CH_3CN$): C, 70.98; H, 4.58; N, 4.41; Cl, 8.51. Found: C, 71.13; H, 4.65; N, 4.51; Cl, 8.67.

Example 20

12-Chloro-15H-benz[b]isoquino[2',1':3,4]imidazo-1,5-d][benzoxazepin-15-one (28)

Compound 28

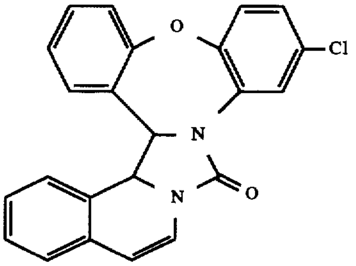

Compound 28 was prepared following the general methodology described in Example 13, except that methylithium was employed as the base, and that isoquinoline was employed as the electrophile. Silica gel purification with 5% ethyl acetate/hexane followed by lyophilization from acetonitrile/water gave 550 mg (43%) of Compound 28 in a single disastereoisomer. $^1$H NMR ($CDCl_3$): δ 8.33 (s, 1H, ArH), 7.40–7.45 (m, 1H, ArH), 7.10–7.33 (m, 8H, ArH), 7.07 (d, J=7 Hz, 1H, ArCH), 6.97 (d, J=8 Hz, 1H, ArH), 6.86 (d, J=8 Hz, 1H, ArH), 6.22 (d, J=11 Hz, 1H, CH=), 6.07 (d, J=7 Hz, 1H, ArCH), 5.35 (d, J=11 Hz, 1H, CH=). FABMS: m/z 393 (M+Li). HRMS calculated for $C_{23}H_{15}N_2O_2LiCl$ (M+Li) 393.0982, found 393.0967. Analysis Calculated for $C_{23}H_{12}N_2O_2Cl$: C, 71.41; H, 3.91; N, 7.24; Cl, 9.16. Found: C, 71.19; H, 4.04; N, 7.18; Cl, 9.84.

Example 21

12-Chloro-17,18-dihydro-15H-benz[b]isoquino[2',1';3,4]-imidazo[1,5-d][1,4]benzoxazepin-15-one (29)

Compound 29

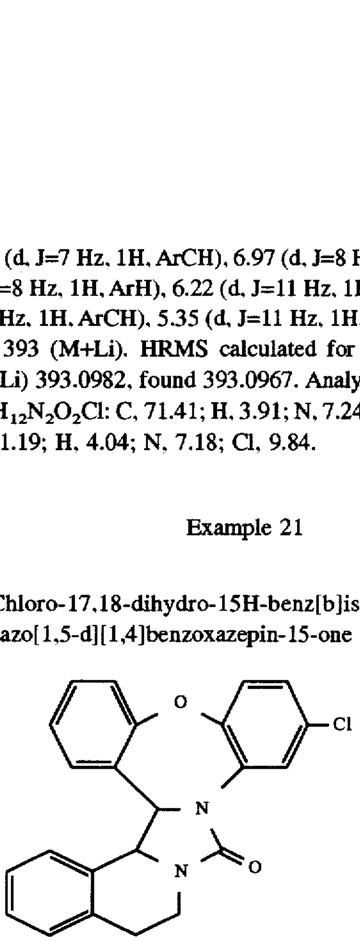

To a solution of 400 mg (1.03 mmol) of Compound 28 in 10 mL of ethanol was added approximately 50 mg of Pd-C catalyst. After flashing with nitrogen several times, the mixture was put on a par shaker for 2 hours under 30 psi of hydrogen gas. The catalyst was removed by filtration. Silica gel purification with 0–10% ethyl acetate/hexane followed by lyophilization from acetonitrile/water gave 290 mg (72%) of Compound 29. $^1$H NMR ($CDCl_3$): δ 8.22 (s, 1H, ArH), 7.52 (d, J=7 Hz, 1H, ArH), 7.36–7.42 (m, 1H, ArH), 7.10–7.35 (m, 7H, ArH), 6.91 (d, J=6 Hz, 1H, ArH), 5.86 (d, J=4 Hz, 1H, ArCH), 5.30 (s, 1H, ArCH), 4.19–4.28 (m, 1H), 3.16–3.40 (m, 2H), 2.78 (d, J=17 Hz, 1H). FABMS: m/z 395 (M+Li). HRMS calculated for $C_{23}H_{17}N_2O_2LiCl$ (M+Li) 395.1139, found 395.1136. Analysis Calculated for $C_{23}H_{17}N_2O_2Cl$: C, 71.04; H, 4.41; N, 7.20; Cl, 9.12. Found: C, 71.06; H, 4.62; N, 7.14; Cl, 8.98.

Example 22

6-Chloro-1-phenyl-2H-dibenz[b,f]imidazo[1,5-d]-[1,4]oxazepin-3-one (30)

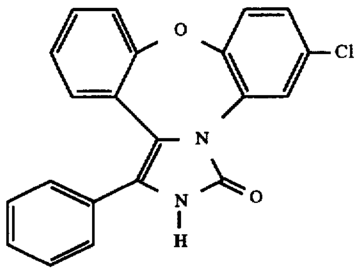

Compound 30

Compound 30 was prepared following the general methodology described in Example 13, except that benzonitrile was employed as the electrophile. Silica gel purification with 20% ethyl acetate/hexane followed by lyophilization from acetonitrile/water gave 467 mg (42%) of Compound 30. $^1$H NMR (mixed $CDCl_3$ and DMSO-$d_6$): δ 10.50 (s, 1H, NH), 7.26–7.28 (m, 1H, ArH), 6.61–6.68 (m, 2H, ArH), 6.46–6.60 (m, 6H, ArH), 6.43 (dd, J=9, 3 Hz, 1H, ArH), 6.36 (d, J=8 Hz, 1H, ArH), 6.22 (t, J=8 Hz, 1H, ArH). EIMS (70 ev): m/z (relative intensity) 360 ($M^+$, 100), 229 (12), 104 (35), 77 (13). HRMS calculated for $C_{21}H_{13}N_2O_2Cl$ ($M^+$) 360.0666, found 360.0689. Analysis Calculated for $C_{21}H_{13}N_2O_2Cl$: C, 69.91; H, 3.63; N, 7.76; Cl, 9.83. Found: C, 69.62; H, 3.82; N, 7.34; Cl, 9.53.

Example 23

6-Chloro-2-methyl-1-phenyl-2H-dibenz[b,f]imidazo-[1,5-d][1,4-oxazepin-3-one (31)

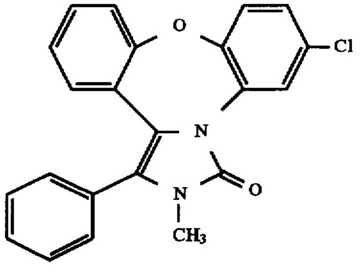

Compound 31

Compound 31 was prepared following the general methodology described in Example 13, except that benzonitrile and iodomethane were employed as the electrophiles. Iodomethane was added at 0° C. forty-five minutes after the complete addition of the benzonitrile. Silica gel purification with 10–20% ethyl acetate/hexane followed by recrystallization from dichloromethane/hexane gave 360 mg (32%) of Compound 31 as a solid, mp 220°–221.5°. $^1$H NMR ($CDCl_3$): δ 8.11 (s, 1H, ArH), 7.40–7.45 (m, 3H, ArH), 7.33–7.40 (m, 2H, ArH), 7.21–7.27 (m, 2H, ArH), 7.18 (dt, J=8, 2 Hz, 2H, ArH), 6.76–6.87 (m, 2H, ArH), 3.27 (s, 3H, $NCH_3$). FABMS: m/z 375 (M+H). HRMS calculated for $C_{22}H_{15}N_2O_2LiCl$ (M+Li) 381.0982, found 381.1050. Analysis Calculated for $C_{22}H_{15}N_2O_2Cl$ (0.12 $CH_2Cl_2$): C, 69.06; H, 3.99; N, 7.28; Cl, 11.35. Found: C, 69.28; H, 4.12; N, 7.23; Cl, 11.51.

Example 24

6-Chloro-1-(2-phenylethyl)-2H-dibenz[b,f]imidazo-[1,5-d][1,4]oxazepin-3-one (32)

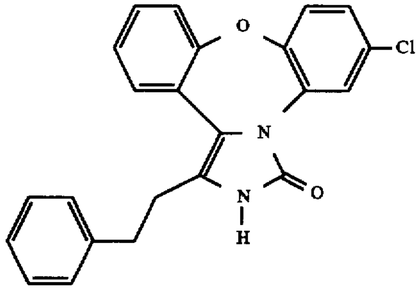

Compound 32

Compound 32 was prepared following the general methodology described in Example 13, except that hydrocinnamonitrile was employed as the electrophile. Silica gel purification with 0–50% ethyl acetate/hexane followed by lyophilization from acetonitrile/water gave 250 mg (21%) of Compound 32. $^1$H NMR ($CDCl_3$): δ 10.00 (s, 1H, NH), 8.06 (s, 1H, ArH), 7.20–7.36 (m, 7H, ArH), 7.07–7.17 (m, 4H, ArH), 2.95–3.07 (m, 4H, $PhCH_2CH_2$). EIMS (70 ev): m/z (relative intensity) 388 (22), 299 (33), 297 (100), 255 (14), 254 (13), 91 (30). HRMS calculated for $C_{23}H_{17}N_2O_2Cl$ ($M^+$) 388.0979, found 388.0993. Analysis Calculated for $C_{23}H_{17}N_2O_2Cl$: C, 71.04 H, 4.41; N, 7.20; Cl, 9.12. Found: C, 71.17; H, 4.43; N, 7.15; Cl, 9.36.

Example 25

6-Chloro-2-phenyl-2,13bH-dibenz[b,f]imidazo-[1,5-d][1,4]oxazepin-1,3-dione (33)

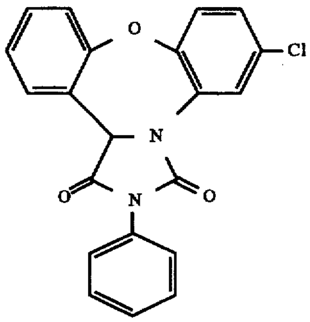

Compound 33

Compound 33 was prepared following the general methodology described in Example 13, except that phenyl isocyanate was employed as the electrophile. Silica gel purification with 2–10% ethyl acetate/hexane followed by lyophilization from acetonitrile/water gave 520 mg (46%) of Compound 33. $^1$H NMR ($CDCl_3$): δ 8.41 (d, J=3 Hz, 1H, ArH), 7.37–7.58 (m, 8H, ArH), 7.22–7.32 (m, 2H, ArH), 7.14 (dd, J=8, 3 Hz, 1H, ArH), 6.14 (s, 1H, ArCH). FABMS: m/z 377 (M+H). HRMS calculated for $C_{21}H_{13}N_3O_3LiCl$ (M+Li) 383.0775, found 383.0806. Analysis Calculated for $C_{21}H_{13}N_2O_3Cl$: C, 66.94; H, 3.48; N, 7.43; Cl, 9.41. Found: C, 67.00; H, 3.51; N, 7.32; Cl, 9.71.

Example 26

6-Chloro-2-phenylmethyl-2H,13bH-dibenz[b,f]-imidazo-[1,5-d][1,4]oxazepin-1,3-dione (34)

Compound 34

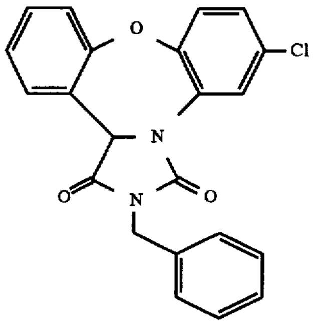

Compound 34 was prepared following the general methodology described in Example 13, except that benzyl isocyanate was employed as the electrophile. Silica gel purification with 2–10% ethyl acetate/hexane followed by recrystallization from diethyl ether/hexane gave 515 mg (44%) of Compound 34 as a solid, mp 82°–84°. $^1H$ NMR ($CDCl_3$): δ 8.44 (d, J=3 Hz, 1H, ArH), 7.42–7.52 (m, 2H, ArH), 7.28–7.40 (m, 5H, ArH), 7.15–7.25 (m, 3H, ArH), 7.07 (dd, J=9, 3 Hz, 1H, ArH), 6.00 (s, 1H, ArCH), 4.84 (s, 2H, $PhCH_2$). FABMS: m/z 391 (M+H). HRMS calculated for $C_{22}H_{15}N_2O_3LiCl$ (M+Li) 397.0931, found 397.0958. Analysis Calculated for $C_{22}H_{15}N_2O_3Cl$: C, 67.61; H, 3.87; N, 7.17; Cl, 9.07. Found: C, 67.71; H, 4.04; N, 7.25; Cl, 9.16.

Example 27

6-Chloro-2-(2-phenylethyl)-2H,13bH-dibenz[b,f]-imidazo [1,5-d][1,4]oxazepin-1,3-dione (35)

Compound 35

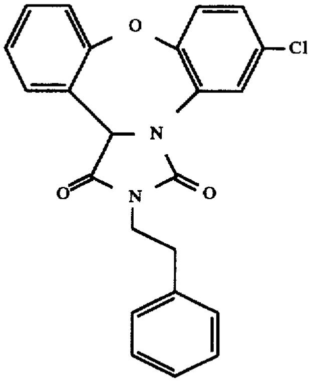

Compound 35 was prepared following the general methodology described in Example 13, except that β-phenyl ethyl isocyanate was employed as the electrophile. Silica gel purification with 2–10% ethyl acetate/hexane followed by lyophilization from acetonitrile/water gave 660 mg (54%) of Compound 35. $^1H$ NMR ($CDCl_3$): δ 8.44 (d, J=3 Hz, 1H, ArH), 7.10–7.40 (m, 10H, ArH), 7.00 (d, J=3 Hz, 1H, ArH), 5.92 (s, 1H, ArCH), 4.00–4.10 (m, 1H, NCH), 3.86–3.95 (m, 1H, NCH), 3.06 (t, J=8 Hz, 2H, $PhCH_2$). FABMS: m/z 411 (M+Li). HRMS calculated for $C_{23}H_{17}N_2O_3LiCl$ (M+Li) 411.1088, found 411.1088. Analysis Calculated for $C_{23}H_{17}N_2O_3Cl$: C, 68.24; H, 4.23; N, 6.92; Cl, 8.76. Found: C, 68.30; H, 4.43; N, 6.79; Cl, 9.15.

The foregoing examples are provided to enable one of ordinary skill in the art to practice the present invention.

These examples are merely illustrative, however, and should not be read as limiting the scope of the invention as it is claimed in the appended claims.

(7) Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn*, 267, 131–140 (1984); C. Vander Wende et al., *Fed. Proc.*, 15, 494 (1956); Koster et al., *Fed. Proc.*, 18, 412 (1959); and Witken et al., *J. Pharmacol. exp. Ther.*, 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table 1 hereinbelow.

Charles River male albino mice, weighing 20 to 30 grams, were used in this assay.

Thirty minutes after intragastric administration to ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 (1974).

The results for the particular compounds of the present invention analyzed in this assay, and discussed in the examples identified below which correspond thereto, are presented in Table 1 hereinbelow as fractions under the heading "WRITHING ASSAY." The fractions indicate the number of mice out of eight or ten in which a test compound produced analgesia.

The standard initial screening dose of a test compound employed in this assay was 30 mpk per gram of body weight. Generally, if this initial screening dose of the test compound produced analgesia in seven out of ten mice, then the effect of additional doses of the test compound on the writhing response was evaluated, and then the $ED_{50}$ dose was generally calculated. (The slopes of the dose-response curves for all test compounds analyzed were compared as described by Tallarida and Murray, *Manual of Pharmacologic Calculations*, Page 11 (Springer Verlag, New York, 1981)).

All $ED_{50}$ doses calculated are also presented in Table 1 hereinbelow under the heading "WRITHING ASSAY," but as whole numbers.

(b) Prostaglandin (PGE) Antagonism Assay

In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound functionally antagonizes prostaglandin $E_2$.

Male albino guinea pigs weighing 200 to 500 grams were sacrificed by cervical dislocation. The ilea were then quickly removed from the guinea pigs and placed in a modified Tyrode solution, a solution which is known to those skilled in the art, containing one-half of the usual amount of magnesium ions.

Segments of ileum about 2 cm long were then cut and mounted in a 10 mL tissue bath containing the modified Tyrode solution. The solution was maintained at 37° C. and aerated with a gaseous mixture of 95% oxygen and 5% carbon dioxide. Data for a control prostaglandin $E_2$ dose response curve plotting concentration of prostaglandin $E_2$ versus the intensity of contractions, detected isotonically, was then obtained by experimentally adjusting the dose of the prostaglandin $E_2$ being injected into the tissue bath, in a manner known by those of skill in the art.

Solutions or suspensions containing an initial concentration (3 micromolar) of a test compound in modified Tyrode solution ("test solutions/suspensions") were then separately substituted for the control bath solution. Each test solution/suspension was then kept in constant contact with the ileum tissue, except for brief periods to drain the bath in preparation for rinsing with fresh test solution/suspension. A second prostaglandin $E_2$ dose response curve was then generated for prostaglandin $E_2$ in the presence of a test compound.

A control dose response curve is produced in isolated segments of guinea pig ileum mounted in an automated apparatus with six concentrations of prostaglandin $E_2$. A solution or suspension of test compound is substituted for the control bathing solution and is incubated for thirty minutes. An additional prostaglandin $E_2$ dose response curve is then performed in the presence of the test compound. A dose ratio is calculated from the $EC_{50}$ values obtained from duplicate replications on each concentration of the test compound. A concentration of test compound is judged to be active if it produces a dose ratio significantly greater than that obtained in a series of blank treatments.

A dose ratio of $EC_{50}$ doses was calculated from the results of each test in a manner known by those of skill in the art, and described above.

The results of this prostaglandin antagonism assay are also presented in Table 1 hereinbelow. The dose ratios reported in Table 1 represent an average of multiple dose ratios for those compounds for which more than one dose ratio was determined. The compounds of the present invention which were tested in this assay, and for which results are presented in Table 1, correspond to the particular examples specified in Table 1.

The $pA_2$ value (a statistical constant which is a common measure of expressing the potency of a particular drug as a competitive antagonist), rather than the dose ratio, was calculated for the test compound shown and described in Example 6 by schild plot calculations, as described by H. O. Schild, "pA, A New Scale for the Measurement of Drug Antagonism," *Br. J. Pharmacol*, 2, 189 (1947), and is reported in Table 1.

TABLE 1

Data Generated from the Assays

| Compound Number and Example Number | | WRITHING ASSAY Number Out of Eight or Ten at 30 mpk or $ED_{50}$ Dose (I.G.) | $PGE_2$ ANTAGONISM IN GUINEA PIG ILEUM Dose Ratio at $3 \times 10^{-6}$M or $PA_2$ Value |
|---|---|---|---|
| Compound 2 | (Example 2) | 1/10 | 29.2 |
| Compound 3 | (Example 2) | 3/10 | 43.6 |
| Compound 4 | (Example 2) | 3/10 | 0.87 |
| Compound 5 | (Example 3) | 10/10; 3.7 | 10.93 |
| compound 5a | (Example 3) | 8/10 | 5.2 |
| Compound 5b | (Example 3) | 4/10 | 80.5 |
| Compound 6 | (Example 3) | 5/10 | $PA_2$ Value = 7.15 |
| Compound 6a | (Example 3) | 2/10 | 23.4 |
| Compound 6b | (Example 3) | 6/10 | 2.7 |
| Compound 7 | (Example 3) | 9/10 | 1.5 |
| Compound 8 | (Example 4) | 5/10 | Not Yet Tested |
| Compounds 9a and 9b (Mixture) | (Example 4) | Not Yet Tested | 1.5 |
| Compound 10 | (Example 5) | 1/10 | 28.94 |
| Compound 11 | (Example 5) | 2/8 | 8.6 |
| Compound 12 | (Example 6) | Not Yet Tested | 1.9 |
| Compound 13 | (Example 7) | Not Yet Tested | 4.4 |
| CompoUnd 16 | (Example 9) | Not Yet Tested | 2.4 |
| Compound 17 | (Example 9) | Not Yet Tested | 2.3 |
| Compound 21 | (Example 13) | Not Yet Tested | 0.9 |
| Compound 22 | (Example 14) | Not Yet Tested | 2.5 |
| Compound 28 | (Example 20) | Not Yet Tested | 3.5 |
| Compound 29 | (Example 21) | Not Yet Tested | 3.8 |
| Compound 30 | (Example 22) | Not Yet Tested | 2.1 |
| Compound 31 | (Example 23) | Not Yet Tested | 1.4 |
| Compound 33 | (Example 25) | Not Yet Tested | 4.3 |
| Compound 34 | (Example 26) | Not Yet Tested | 3.6 |

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound having a structure:

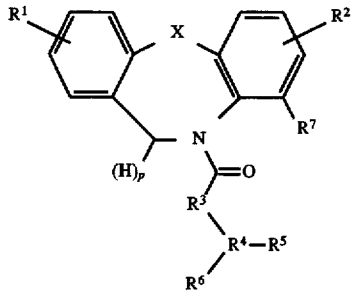

or a pharmaceutically-acceptable salt thereof, wherein:

X is oxygen, sulfur,

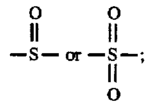

$R^1$, $R^2$ and $R^7$ may be the same or different and are hydrogen or halogen;

$R^3$ is oxygen,

—NH—, —N-alkyl, —N-aryl, —N-alkylenearyl or —N—, and can combine with $R^4$ and $R^5$ to form

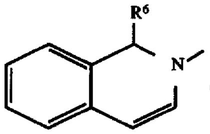 or 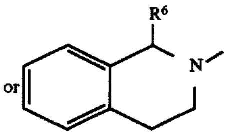 ;

$R^4$ is carbon or —CH—, and can combine with $R^5$ to form carbonyl, a 4-, 5- or 6-membered nonaromatic, saturated, single-ring structure,

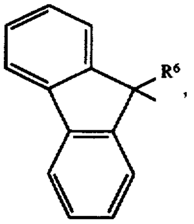 ,

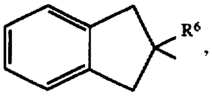 ,

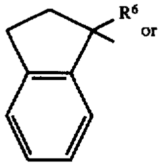 or

-continued

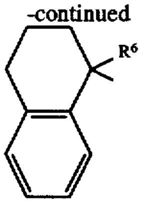 , and can combine with $R^3$ and $R^5$ to form

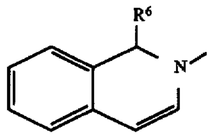 or 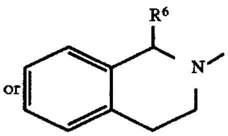 ;

$R^5$ is $—(CH_2)_m—$, oxygen, aryl, aralkyl, arylcarbonylhydroxy, arylcarbonylalkoxy, a mono- or di-valent alkylenearyl or a mono- or divalent alkenylenearyl, and can combine with $R^4$ to form carbonyl, a 4-, 5- or 6-membered nonaromatic, saturated, single-ring structure,

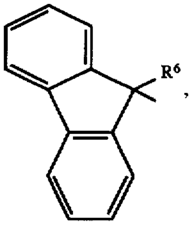 ,

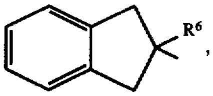 ,

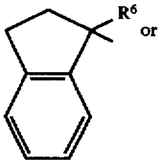 or

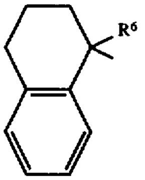 , and can combine with $R^3$ and $R^4$ to form

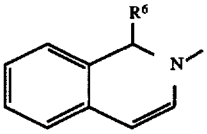 or 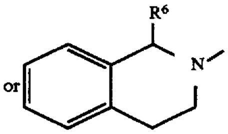 ;

$R^6$ is a single or double covalent bond to the carbon 11 of said compound;

p is 0 or 1; and m is 3, 4 or 5.

2. A compound of claim 1 wherein X is oxygen.

3. A compound of claim 2 wherein $R^1$ is hydrogen.

4. A compound of claim 3 wherein $R_2$ is halogen.

5. A compound of claim 4 wherein $R^3$ is oxygen,

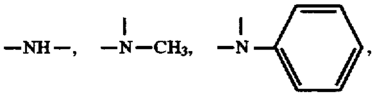

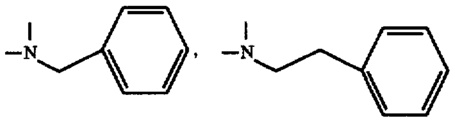

or

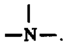

6. A compound of claim 5 wherein $R^5$ is:

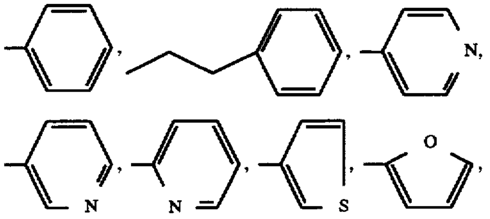

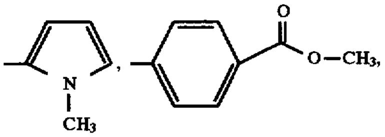

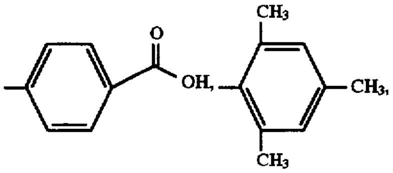

or combines with $R^4$ to form

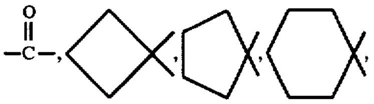

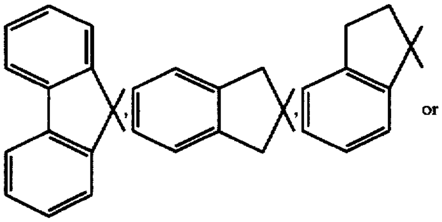

or

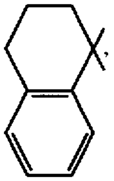

or combines with $R^3$ and $R^4$ to form

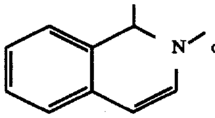

or

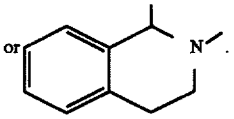

7. A compound of claim 1, wherein the compound is:

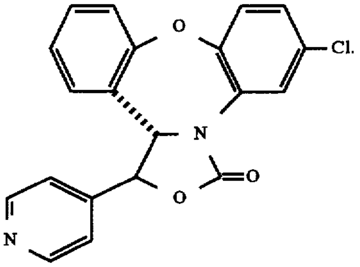

8. A compound of claim 1, wherein the compound is:

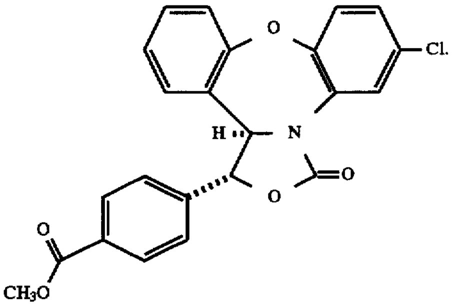

9. A compound claim 1, wherein the compound is:

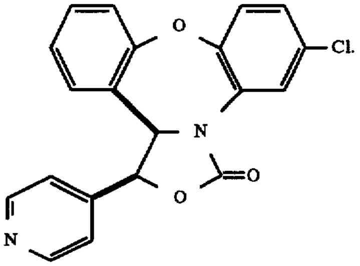

10. A mixture of the following compounds:

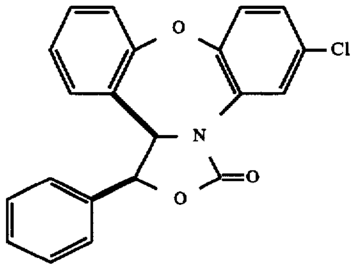

-continued
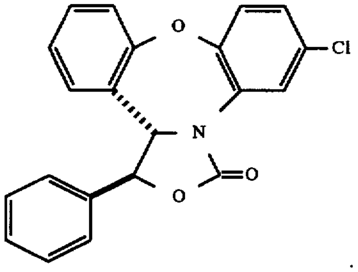
11. A mixture of the following compounds:
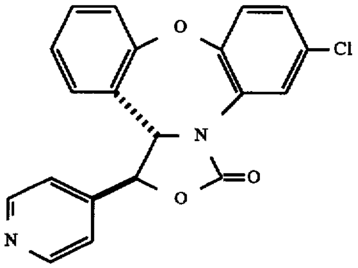
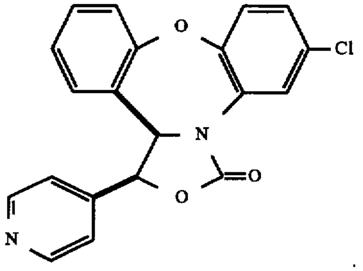
12. A mixture of the following compounds:
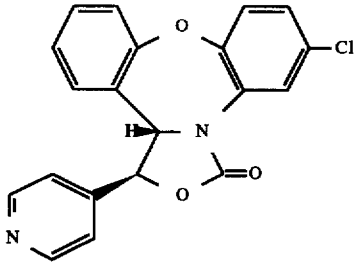
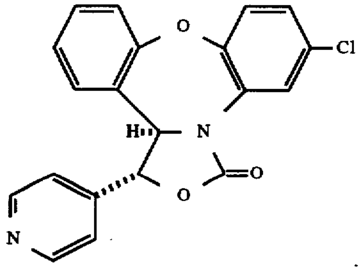
13. A mixture of the following compounds:
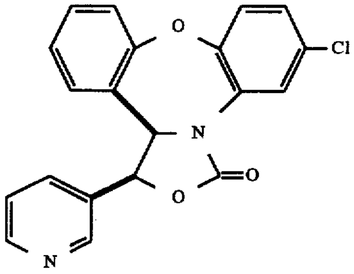
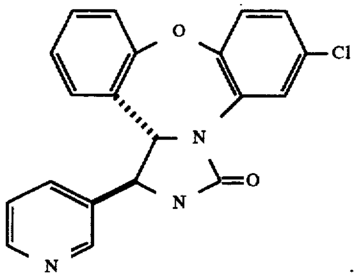
14. A mixture of the following compounds:
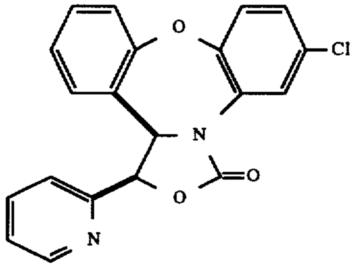
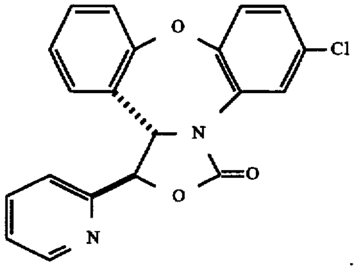
15. A mixture of the following compounds:
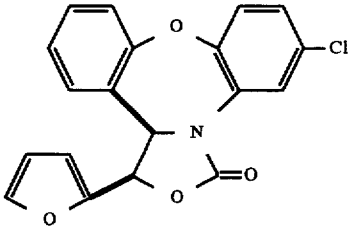

-continued

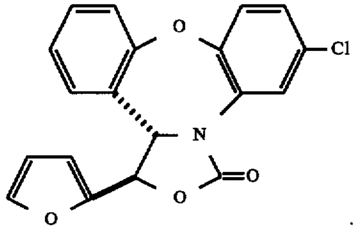

16. A mixture of the following compounds:

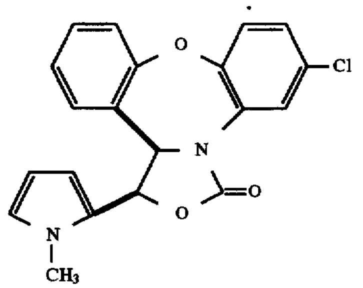

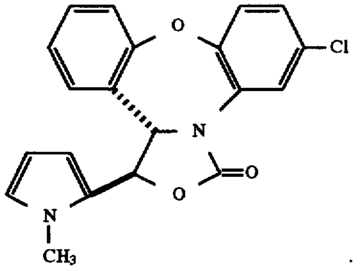

17. A mixture of the following compounds:

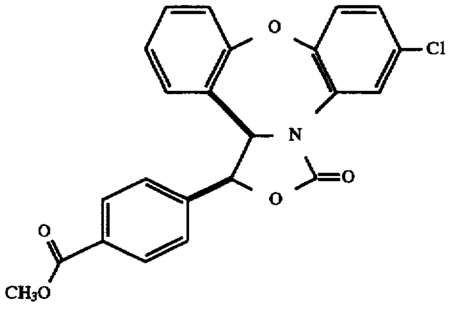

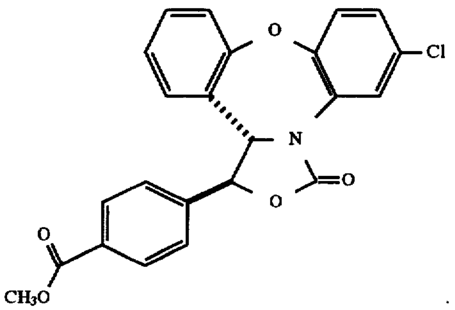

18. A mixture of the following compounds:

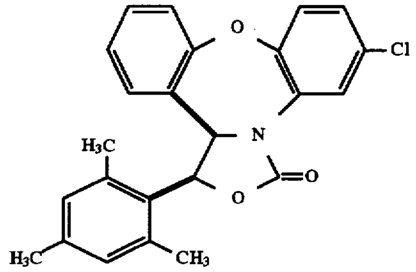

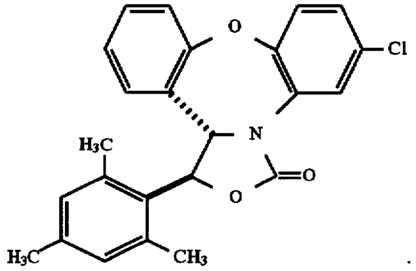

19. A compound of claim 1, wherein the compound is:

6-chloro-1,13b-dihydro-1-phenyl-3H-dibenz[b,f]-oxazolo[3,4d][1,4]oxazepin-3-one (3);

6-chloro-1,13b-dihydro-1-phenyl-3H-dibenz[b,f]-oxazolo-[3,4-d][1,4]oxazepin-3-one (4);

trans-6-chloro-1,13b-dihydro-1-(4-pyridyl)-3H-dibenz-[b,f]oxazolo[3,4-d][1,4]oxazepin-3-one (6);

(+)-trans-6-chloro-1,13b-dihydro-1-(4-pyridyl)-3H-dibenz[b,f]oxazolo[3,4-d][1,4]oxazepin-3-one (6a);

(−)-trans-6-chloro-1,13b-dihydro-1-(4-pyridyl)-3H-dibenz[b,f]oxazolo-[3,4-d][1,4]-oxazepin-3-one (6b);

cis-6-chloro-1,13b-dihydro-1-(4-pyridyl)-3H-dibenz-[b,f]oxazolo-[3,4-d][1,4]oxazepin-3-one (7);

6-chloro-1,13b-dihydro-1-(3-pyridyl)-3H-dibenz[b,f]-oxazolo[3,4-d][1,4]-oxazepin-3-one (9a);

6-chloro-1,13b-dihydro-1-(3-pyridyl)-3H-dibenz[b,f]-oxazolo-[3,4-d][1,4]oxazepin-3-one (9b);

6-chloro-1,13b-dihydro-1-(2-pyridyl)-3H-dibenz-[b,f] oxazolo[3,4-d][1,4]oxazepin-3-one (10);

cis-6-chloro-1,13b-dihydro-1-(2-pyridyl)-3H-dibenz[b,f] oxazolo[3,4-d][1,4]-oxazepin-3-one (11);

6-chloro-1,13b-dihydro-1-(3-thienyl)-3H-dibenz[b,f] oxazolo[3,4-d][1,4-oxazepin-3-one (12);

6-chloro-1,13b-dihydro-1-(-2-furyl)-3H-dibenz[b,f]-oxazolo-[3,4-d][1,4]oxazepin-3-one (14a);

6-chloro-1,13b-dihydro-1-(-2-furyl)-3H-dibenz[b,f]-oxazolo[3,4-d][1,4]-oxazepin-3-one (14b);

6-chloro-1,13b-dihydro-1-(-N-methylpyrryl)-3H-dibenz-[b,f]-oxazolo[3,4-d][1,4]oxazepin-3-one (15a);

6-chloro-1,13b-dihydro-1-(-N-methylpyrryl)-3H-dibenz-[b,f]oxazolo-[3,4-d][1,4]oxazepin-3-one (15b);

6-chloro-1,13b-dihydro-1-(4-carboxymethylphenyl)-3H-dibenz[b,f]-oxazolo[3,4-d][1,4]oxazepin-3-one (16);

6-chloro-1,13b-dihydro-1-(4-carboxymethylphenyl)-3H-dibenz[b,f]-oxazolo[3,4-d][1,4]oxazepin-3-one (17);

6-chloro-1,13b-dihydro-1-(4-carboxylic acid phenyl)-3H-dibenz[b,f]oxazolo[3,4-d][1,4]-oxazepin-3-one (18);

6-chloro-1,13b-dihydro-1-(phenyl)-3-(methyl)-dibenz[b,f]-imidazolo[3,4-d][1,4-oxazepin-3-one (19);

6-Chloro-1,13b-dihydro-1-[2,4,6-trimethyl]phenyl-3H-dibenz[b,f]oxazolo[3,4-d][1,4]oxazepin-3-one (20a);

6-chloro-1,13b-dihydro-1-[2,4,6-trimethyl]-phenyl-3H-dibenz[b,f]oxazolo[3,4-d][1,4]-oxazepin-3-one (20b);

6-Chloro-1,13b-dihydro-3H-spiro[dibenz[b,f]oxazolo[3,4-d][1,4]oxazepin-1,1'-cyclobutan]-3-one (21);

6-Chloro-1,13b-dihydro-3H-spiro[dibenz[b,f]-oxazolo[3,4-d][1,4]oxazepin-1,1'-cyclopentane]-3-one (22);

6-Chloro-1,13b-dihydro-3H-spiro[dibenz[b,f]-oxazolo[3,4-d][1,4]oxazepin-1,1'-cyclohexan]-3-one (23);

6-Chloro-1,13b-dihydro-3H,9'H-spiro[dibenz[b,f]-oxazolo-[3,4-d][1,4]oxazepin-1,9'-fluoren]-3-one (24);

6-Chloro-1,13b-dihydro-3H-spiro[dibenz[b,f]oxazolo-[3,4-d][1,4]oxazepin-1,2'-indan]-3-one (25);

6-Chloro-1,13b-dihydro-3H-spiro[dibenz[b,f]oxazolo-[3,4-d][1,4]oxazepin-1,1'-indan]-3-one (26a);

6-Chloro-1,13b-dihydro-3H-spiro[dibenz[b,f]-oxazolo[3,4-d][1,4]oxazepin-1,1'-indan]-3-one (26b);

6-Chloro-1,1',2',3',4'-13b-hexahydro-3H-spiro[dibenz-[b,f]oxazolo[3,4-d][1,4]oxazepin-1,1'-naphthalen]-3-one (27a);

6-Chloro-1,1',2',3',4'-13b-hexahydro-3H-spiro-[dibenz[b,f]oxazolo[3,4-d][1,4]oxazepin-1,1'-naphthalen]-3-one (27b);

12-Chloro-15H-benz[b]isoquino[2',1':3,4]imidazo-[1,5-d][1–4]benzoxazepin-15-one (28);

12-Chloro-17,18-dihydro-15H-benz[b]isoquino-[2',1':3,4]imidazo[1,5-d][1,4]-benzoxazepin-15-one (29);

6-Chloro-1-phenyl-2H-dibenz[b,f]imidazo[1,5-d]-[1,4]oxazepin-3-one (30);

6-Chloro-2-methyl-1-phenyl-2H-dibenz[b,f]imidazo-[1,5-d][1,4]oxazepin-3-one (31);

6-Chloro-2-phenyl-2,13bH-dibenz[b,f]imidazo-1,5-d][1,4]oxazepin-1,3-dione (33);

6-Chloro-2-(phenylmethyl)-2H,13bH-dibenz[b,f]-imidazo[1,5-d][1,4]oxazepin-1,3-dione (34); or 6-Chloro-2-(2-phenylethyl)-2H,13bH-dibenz[b,f]-imidazo[1,5-d][1,4]oxazepin-1,3-dione (35).

20. A pharmaceutical composition comprising a pharmaceutically-acceptable carrier and a therapeutically-effective amount of a compound having a structure:

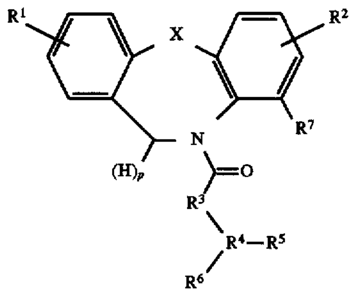

or a pharmaceutically-acceptable salt thereof, wherein:

X is oxygen, sulfur, $$-\overset{\overset{O}{\|}}{S}- \text{ or } -\underset{\underset{O}{\|}}{\overset{\overset{O}{\|}}{S}}-;$$

$R^1$, $R^2$, and $R^7$ may be the same or different and are hydrogen or halogen;

$R^3$ oxygen, $$-NH-,\ -\underset{|}{N}\text{-alkyl},\ -\underset{|}{N}\text{-aryl},\ -\underset{|}{N}\text{-alkylenearyl or } -\underset{|}{N}-,$$

and can combine with $R^4$ and $R^5$ to form

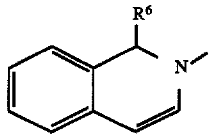 or 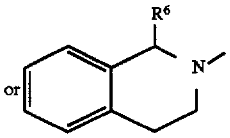;

$R^4$ is carbon or —CH—, and can combine with $R^5$ to form carbonyl, a 4-, 5- or 6-membered nonaromatic, saturated, single-ring structure,

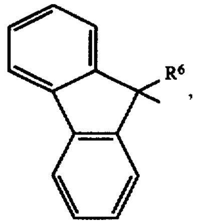,

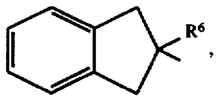,

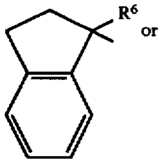 or

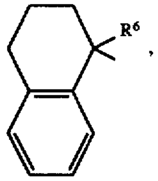, and can combine with $R^3$ and $R^5$ to form

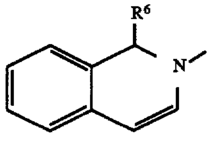 or 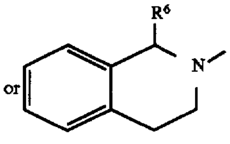;

$R^5$ is $-(CH_2)_m-$, oxygen, aryl, aralkyl, arylcarbonylhydroxy, arylcarbonylalkoxy, a mono- or di-valent alkylenearyl or a mono- or divalent alkenylenearyl, and can combine with $R^4$ to form carbonyl, a 4-, 5- or 6-membered nonaromatic, saturated, single-ring structure,

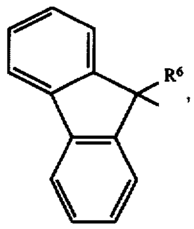

,

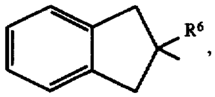

,

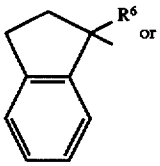

or

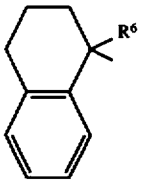

, and can combine with $R^3$ and $R^4$ to form

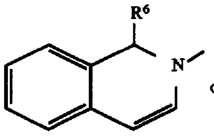

or

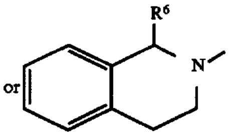

;

$R^6$ is a single or double covalent bond to the carbon 11 of said compound;

p is 0 or 1; and m is 3, 4 or 5.

21. The pharmaceutical composition of claim 20 wherein the compound is:

6-chloro-1,13b-dihydro-1-phenyl-3H-dibenz[b,f]-oxazolo[3,4d][1,4oxazepin-3-one (3);

6-chloro-1,13b-dihydro-1-phenyl-3H-dibenz[b,f]-oxazolo-[3,4-d][1,4oxazepin-3-one (4);

trans-6-chloro-1,13b-dihydro-1-(4-pyridyl)-3H-dibenz-[b,f]oxazolo[3,4-d][1,4]oxazepin-3-one (6);

(+)-trans-6-chloro-1,13b-dihydro-1-(4-pyridyl)-3H-dibenz[b,f]oxazolo[3,4-d][1,4]oxazepin-3-one (6a);

(−)-trans-6-chloro-1,13b-dihydro-1-(4-pyridyl)-3H-dibenz[b,f]oxazolo-[3,4-d][1,4]-oxazepin-3-one (6b);

cis-6-chloro-1,13b-dihydro-1-(4-pyridyl)-3H-dibenz-[b,f]oxazolo-[3,4-d][1,4]oxazepin-3-one (7);

6-chloro-1,13b-dihydro-1-(3-pyridyl)-3H-dibenz[b,f]-oxazolo[3,4-d][1,4]-oxazepin-3-one (9a);

6-chloro-1,13b-dihydro-1-(3-pyridyl)-3H-dibenz[b,f]-oxazolo-[3,4-d][1,4]oxazepin-3-one (9b);

6-chloro-1,13b-dihydro-1-(2-pyridyl)-3H-dibenz-]b,f] oxazolo[3,4-d][1,4]oxazepin-3-one (10);

cis-6-chloro-1,13b-dihydro-1-(2-pyridyl)-3H-dibenz[b,f] oxazolo[3,4-d][1,4]-oxazepin-3-one (11);

6-chloro-1,13b-dihydro-1-(3-thienyl)-3H-dibenz[b,f] oxazolo[3,4-d][1,4]-oxazepin-3-one (12);

6-chloro-1,13b-dihydro-1-(-2-furyl)-3H-dibenz[b,f]-oxazolo-[3,4-d][1,4]oxazepin-3-one (14a);

6-chloro-1,13b-dihydro-1-(-2-furyl)-3H-dibenz[b,f]-oxazolo[3,4-d][1,4]-oxazepin-3-one (14b);

6-chloro-1,13b-dihydro-1-(-N-methylpyrryl)-3H-dibenz-[b,f]-oxazolo[3,4-d][1,4]oxazepin-3-one (15a);

6-chloro-1,13b-dihydro-1-(-N-methylpyrryl)-3H-dibenz-[b,f]oxazolo-[3,4-d][1,4]oxazepin-3-one (15b);

6-chloro-1,13b-dihydro-1-(4-carboxymethylphenyl)-3H-dibenz[b,f]-oxazolo[3,4-d][1,4]oxazepin-3-one (16);

6-chloro-1,13b-dihydro-1-(4-carboxymethylphenyl)-3H-dibenz[b,f]-oxazolo[3,4-d][1,4]oxazepin-3-one (17);

6-chloro-1,13b-dihydro-1-(4-carboxylic acid phenyl)-3H-dibenz[b,f]oxazolo[3,4-d][1,4]-oxazepin-3-one (18);

6-chloro-1,13b-dihydro-1-(phenyl)-3-(methyl)-dibenz[b,f]-imidazolo[3,4-d][1,4-oxazepin-3-one (19);

6-Chloro-1,13b-dihydro-1-[2,4,6-trimethyl]phenyl-3H-dibenz[b,f]oxazolo[3,4-d][1,4]oxazepin-3-one (20a);

6-chloro-1,13b-dihydro-1-[2,4,6-trimethyl]-phenyl-3H-dibenz[b,f]oxazolo[3,4-d][1,4]-oxazepin-3-one (20b);

6-Chloro-1,13b-dihydro-3H-spiro[dibenz[b,f]oxazolo[3,4-d][1,4]oxazepin-1,1'-cyclobutan]-3-one (21);

6-Chloro-1,13b-dihydro-3H-spiro[dibenz[b,f]-oxazolo[3,4-d][1,4]oxazepin-1,1'-cyclopentan]-3-one (22);

6-Chloro-1,13b-dihydro-3H-spiro[dibenz[b,f]-oxazolo[3,4-d][1,4]oxazepin-1,1'-cyclohexan]-3-one (23);

6-Chloro-1,13b-dihydro-3H,9'H-spiro[dibenz[b,f]-oxazolo-[3,4-d][1,4]oxazepin-1,9'-fluoren]-3-one (24);

6-Chloro-1,13b-dihydro-3H-spiro[dibenz[b,f]oxazolo-[3,4-d][1,4]oxazepin-1,2'-indan]-3-one (25);

6-Chloro-1,13b-dihydro-3H-spiro[dibenz[b,f]oxazolo-[3,4-d][1,4]oxazepin-1,1'-indan]-3-one (26a);

6-Chloro-1,13b-dihydro-3H-spiro[dibenz[b,f]-oxazolo[3,4-d][1,4]oxazepin-1,1'-indan]-3-one (26b);

6-Chloro-1,1',2',3',4'-13b-hexahydro-3H-spiro[dibenz-b,f]oxazolo[3,4-d][1,4]oxazepin-1,1'-naphthalen]-3-one (27a);

6-Chloro-1,1',2',3',4'-13b-hexahydro-3H-spiro-[dibenz[b,f]oxazolo[3,4-d][1,4]oxazepin-1,1'-naphthalen]-3-one (27b);

12-Chloro-15H-benz[b]isoquino[2',1':3,4]imidazo-[1,5-d][1–4]benzoxazepin-15-one (28);

12-Chloro-17,18-dihydro-15H-benz[b]isoquino-[2',1':3,4]imidazo[1,5-d][1,4]-benzoxazepin-15-one (29);

6-Chloro-1-phenyl-2H-dibenz[b,f]imidazo[1,5-d]-[1,4] oxazepin-3-one (30);

6-Chloro-2-methyl-1-phenyl-2H-dibenz[b,f]imidazo-[1,5-d][1,4]oxazepin-3-one (31);

6-Chloro-2-phenyl-2,13bH-dibenz[b,f]imidazo-[1,5-d][1,4]oxazepin-1,3-dione (33);

6-Chloro-2-(phenylmethyl)-2H,13bH-dibenz[b,f]-imidazo[1,5-d][1,4]oxazepin-1,3-dione (34); or 6-Chloro-2-(2-phenylethyl)-2H,13bH-dibenz[b,f]-imidazo[1,5-d][1,4]oxazepin-1,3-dione (35).

22. The composition of claim 21 wherein the compound is:

trans-6-chloro-1,13b-dihydro-1-(4-pyridyl)-3H-dibenz-[b,f]oxazolo[3,4-d][1,4]oxazepin-3-one (6);

(−)-trans-6-chloro-1,13b-dihydro-1-(4-pyridyl)-3H-dibenz[b,f]oxazolo-[3,4-d][1,4]-oxazepin-3-one (66); or cis-6-chloro-1,13b-dihydro-1-(4-pyridyl)-3H-dibenz-[b,f]oxazolo-[3,4-d][1,4]oxazepin-3-one (7).

23. A method for treating pain in an animal comprising administering to said animal a therapeutically-effective amount of a compound having a structure:

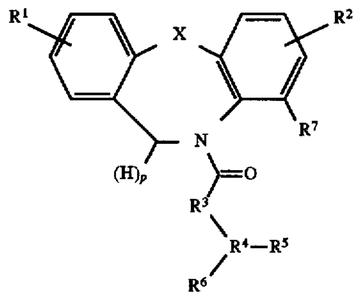

or a pharmaceutically-acceptable salt thereof, wherein:

X is oxygen, sulfur,

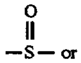 or 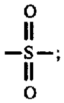;

$R^1$, $R^2$ and $R^7$may be the same or different and are hydrogen or halogen;

$R^3$ is oxygen,

—NH—, —N-alkyl, —N-aryl, —N-alkylenearyl or —N—, and can combine with $R^4$ and $R^5$ to form

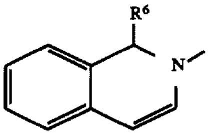 or 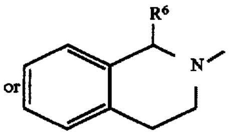 ;

$R^4$ is carbon or —CH—, and can combine with $R^5$ to form carbonyl, a 4-, 5- or 6-membered nonaromatic, saturated, single-ring structure,

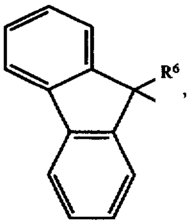 ,

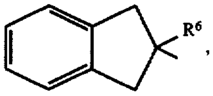 ,

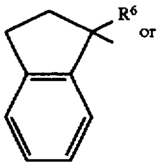 or

-continued

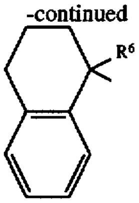 , and can combine with $R^3$ and $R^5$ to form

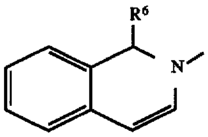 or 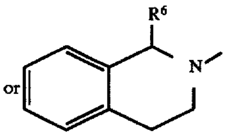 ;

$R^5$ is $—(CH_2)_m—$, oxygen, aryl, aralkyl, arylcarbonylhydroxy, arylcarbonylalkoxy, a mono- or di-valent alkylenearyl or a mono- or divalent alkenylenearyl, and can combine with $R^4$ to form carbonyl, a 4-, 5- or 6-membered nonaromatic, saturated, single-ring structure,

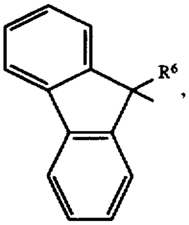 ,

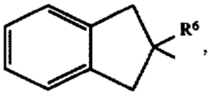 ,

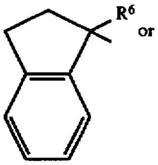 or

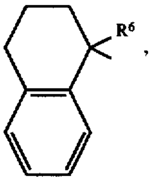 , and can combine with $R^3$ and $R^4$ to form

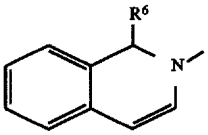 or 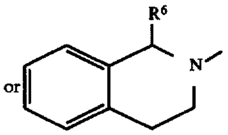 ;

$R^6$ is a single or double covalent bond to the carbon 11 of said compound;

p is 0 or 1; and m is 3, 4 or 5.

24. The method of claim 23 wherein the compound is:

6-chloro-1,13b-dihydro-1-phenyl-3H-dibenz[b,f]-oxazolo[3,4d][1,4]oxazepin-3-one (3);

6-chloro-1,13b-dihydro-1-phenyl-3H-dibenz[b,f]-oxazolo-[3,4-d][1,4]oxazepin-3-one (4);

trans-6-chloro-1,13b-dihydro-1-(4-pyridyl)-3H-dibenz-[b,f]oxazolo[3,4-d][1,4]oxazepin-3-one (6);

(+)-trans-6-chloro-1,13b-dihydro-1-(4-pyridyl)-3H-dibenz[b,f]oxazolo[3,4-d][1,4]oxazepin-3-one (6a);

(−)-trans-6-chloro-1,13b-dihydro-1-(4-pyridyl)-3H-dibenz[b,f]oxazolo-[3,4-d][1,4]-oxazepin-3-one (6b);

cis-6-chloro-1,13b-dihydro-1-(4-pyridyl)-3H-dibenz-[b,f]oxazolo-[3,4-d][1,4]oxazepin-3-one (7);

6-chloro-1,13b-dihydro-1-(3-pyridyl)-3H-dibenz[b,f]-oxazolo[3,4-d][1,4]-oxazepin-3-one (9a);

6-chloro-1,13b-dihydro-1-(3-pyridyl)-3H-dibenz[b,f]-oxazolo-[3,4-d][1,4]oxazepin-3-one (9b);

6-chloro-1,13b-dihydro-1-(2-pyridyl)-3H-dibenz-[b,f]-oxazolo-[3,4-d][1,4]oxazepin-3-one (9b);

cis-6-chloro-1,13b-dihydro-1-(2-pyridyl)-3H-dibenz[b,f] oxazolo[3,4-d][1,4]-oxazepin-3-one (11);

6-chloro-1,13b-dihydro-1-(3-thienyl)-3H-dibenz[b,f] oxazolo[3,4-d][1,4]-oxazepin-3-one (12);

6-chloro-1,13b-dihydro-1-(-2-furyl)-3H-dibenz[b,f]-oxazolo-[3,4-d][1,4]oxazepin-3-one (14a);

6-chloro-1,13b-dihydro-1-(-2-furyl)-3H-dibenz[b,f]-oxazolo[3,4-d][1,4]-oxazepin-3-one (14b);

6-chloro-1,13b-dihydro-1-(-N-methylpyrryl)-3H-dibenz-[b,f]-oxazolo[3,4-d][1,4]oxazepin-3-one (15a);

6-chloro-1,13b-dihydro-1-(-N-methylpyrryl)-3H-dibenz-[b,f]oxazolo-[3,4-d][1,4]oxazepin-3-one (15b);

6-chloro-1,13b-dihydro-1-(4-carboxymethylphenyl)-3H-dibenz[b,f]-oxazolo[3,4-d][1,4]oxazepin-3-one (16);

6-chloro-1,13b-dihydro-1-(4-carboxymethylphenyl)-3H-dibenz[b,f]-oxazolo[3,4-d][1,4]oxazepin-3-one (17);

6-chloro-1,13b-dihydro-1-(4-carboxylic acid phenyl)-3H-dibenz[b,f]oxazolo[3,4-d][1,4]-oxazepin-3-one (18);

6-chloro-1,13b-dihydro-1-(phenyl)-3-(methyl)-dibenz[b,f]-imidazolo[3,4-d][1,4-oxazepin-3-one (19);

6-Chloro-1,13b-dihydro-1-[2,4,6-trimethyl]phenyl-3H-dibenz[b,f]oxazolo[3,4-d][1,4]oxazepin-3-one (20a);

6-chloro-1,13b-dihydro-1-[2,4,6-trimethyl]-phenyl-3H-dibenz[b,f]oxazolo[3,4-d][1,4]-oxazepin-3-one (20b);

6-Chloro-1,13b-dihydro-3H-spiro[dibenz[b,f]oxazolo[3,4-d][1,4]oxazepin-1,1'-cyclobutan]-3-one (21);

6-Chloro-1,13b-dihydro-3H-spiro[dibenz[b,f]-oxazolo[3,4-d][1,4]oxazepin-1,1'-cyclopentan]-3-one (22);

6-Chloro-1,13b-dihydro-3H-spiro[dibenz[b,f]-oxazolo[3,4-d][1,4]oxazepin-1,1'-cyclohexan]-3-one (23);

6-Chloro-1,13b-dihydro-3H,9'H-spiro[dibenz[b,f]-oxazolo-[3,4-d][1,4]oxazepin-1,9'-fluoren]-3-one (24);

6-Chloro-1,13b-dihydro-3H-spiro[dibenz[b,f]oxazolo-[3,4-d][1,4]oxazepin-1,2'-indan]-3-one (25);

6-Chloro-1,13b-dihydro-3H-spiro[dibenz[b,f]oxazolo-[3,4-d][1,4]oxazepin-1,1'-indan]-3-one (26a);

6-Chloro-1,13b-dihydro-3H-spiro[dibenz[b,f]-oxazolo[3,4-d][1,4]oxazepin-1,1'-indan]-3-one (26b);

6-Chloro-1,1',2',3',4'-13b-hexahydro-3H-spiro[dibenz-[b,f]oxazolo[3,4-d][1,4]oxazepin-1,1'-naphthalen]-3-one (27a);

6-Chloro-1,1',2',3',4'-13b-hexahydro-3H-spiro-[dibenz[b,f]oxazolo[3,4-d][1,4]oxazepin-1,1'-naphthalen]-3-one (27b);

12-Chloro-15H-benz[b]isoquino[2',1':3,4]imidazo-[1,5-d][1–4]benzoxazepin-15-one (28);

12-Chloro-17,18-dihydro-15H-benz[b]isoquino-[2',1':3,4]imidazo[1,5-d][1,4]-benzoxazepin-15-one (29);

6-Chloro-1-phenyl-2H-dibenz[b,f]imidazo[1,5-d]-[1,4] oxazepin-3-one (30);

6-Chloro-2-methyl-1-phenyl-2H-dibenz[b,f]imidazo-[1,5-d][1,4]oxazepin-3-one (31);

6-Chloro-2-phenyl-2,13bH-dibenz[b,f]imidazo-[1,5-d][1,4]oxazepin-1,3-dione (33);

6-Chloro-2-(phenylmethyl)-2H,13bH-dibenz[b,f]-imidazo[1,5-d][1,4]oxazepin-1,3-dione (34); or 6-Chloro-2-(2-phenylethyl)-2H,13bH-dibenz[b,f]-imidazo[1,5-d][1,4]oxazepin-1,3-dione (35).

25. The method of claim 24 wherein the compound is:

trans-6-chloro-1,13b-dihydro-1-(4-pyridyl)-3H-dibenz-[b,f]oxazolo[3,4-d][1,4]oxazepin-3-one (6);

(−)-trans-6-chloro-1,13b-dihydro-1-(4-pyridyl)-3H-dibenz[b,f]oxazolo-[3,4-d][1,4]-oxazepin-3-one (6b); or cis-6-chloro-1,13b-dihydro-1-(4-pyridyl)-3H-dibenz-[b,f]oxazolo-[3,4-d][1,4]oxazepin-3-one (7).

26. A method for treating prostaglandin-$E_2$ mediated diseases in an animal comprising administering to said animal a therapeutically-effective amount of a compound having a structure:

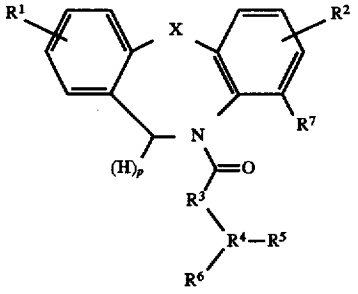

or a pharmaceutically-acceptable salt thereof, wherein:

X is oxygen, sulfur,

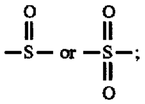

$R^1$, $R^2$ and $R^7$ may be the same or different and are hydrogen or halogen;

$R^3$ is oxygen,

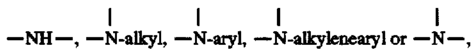

and can combine with $R^4$ and $R^5$ to form

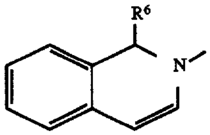

or

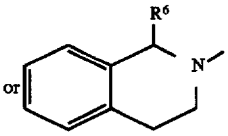

;

$R^4$ is carbon or —CH—, and can combine with $R^5$ to form carbonyl, a 4-, 5- or 6-membered nonaromatic, saturated, single-ring structure,

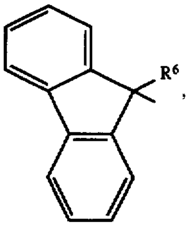

,

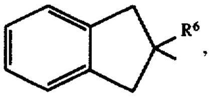

,

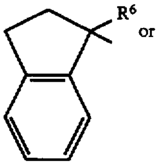

or

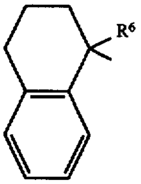

, and can combine with $R^3$ and $R^5$ to form

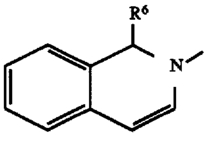

or

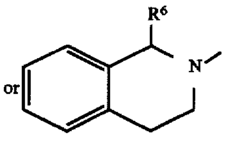

;

$R^5$ is $-(CH_2)_m-$, oxygen, aryl, aralkyl, arylcarbonylhydroxy, arylcarbonylalkoxy, a mono- or di-valent alkylenearyl or a mono- or divalent alkenylenearyl, and can combine with $R^4$ to form carbonyl, a 4-, 5- or 6-membered nonaromatic, saturated, single-ring structure,

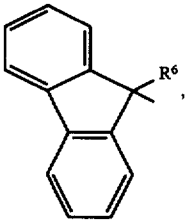

,

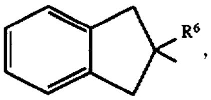

,

-continued

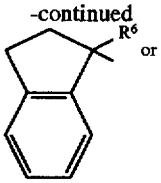

or

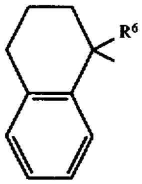

, and can combine with $R^3$ and $R^4$ to form

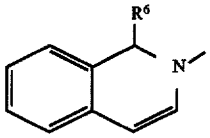

or

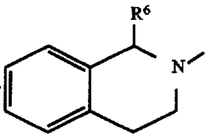

;

$R^6$ is a single or double covalent bond to the carbon 11 of said compound;

p is 0 or 1; and m is 3, 4 or 5.

27. The method of claim 26 wherein the compound is:

6-chloro-1,13b-dihydro-1-phenyl-3H-dibenz[b,f]-oxazolo[3,4-d][1,4oxazepin-3-one (3);

6-chloro-1,13b-dihydro-1-phenyl-3H-dibenz[b,f]-oxazolo-[3,4-d][1,4]oxazepin-3-one (4);

trans-6-chloro-1,13b-dihydro-1-(4-pyridyl)-3H-dibenz-[b,f]oxazolo[3,4-d][1,4]oxazepin-3-one (6);

(+)-trans-6-chloro-1,13b-dihydro-1-(4-pyridyl)-3H-dibenz[b,f]oxazolo[3,4-d][1,4]oxazepin-3-one (6a);

(−)-trans-6-chloro-1,13b-dihydro-1-(4-pyridyl)-3H-dibenz[b,f]oxazolo-[3,4-d][1,4]-oxazepin-3-one (6b);

cis-6-chloro-1,13b-dihydro-1-(4-pyridyl)-3H-dibenz-[b,f]oxazolo-[3,4-d][1,4]oxazepin-3-one (7);

6-chloro-1,13b-dihydro-1-(3-pyridyl)-3H-dibenz[b,f]-oxazolo[3,4-d][1,4]-oxazepin-3-one (9a);

6-chloro-1,13b-dihydro-1-(3-pyridyl)-3H-dibenz[b,f]-oxazolo-[3,4-d][1,4]oxazepin-3-one (9b);

6-chloro-1,13b-dihydro-1-(2-pyridyl)-3H-dibenz-[b,f] oxazolo[3,4-d][1,4]oxazepin-3-one (10);

cis-6-chloro-1,13b-dihydro-1-(2-pyridyl)-3H-dibenz[b,f] oxazolo[3,4-d][1,4]-oxazepin-3-one (11);

6-chloro-1,13b-dihydro-1-(3-thienyl)-3H-dibenz[b,f] oxazolo[3,4-d][1,4]-oxazepin-3-one (12);

6-chloro-1,13b-dihydro-1-(-2-furyl)-3H-dibenz[b,f]-oxazolo-[3,4-d][1,4]oxazepin-3-one (14a);

6-chloro-1,13b-dihydro-1-(-2-furyl)-3H-dibenz[b,f]-oxazolo[3,4-d][1,4]-oxazepin-3-one (14b);

6-chloro-1,13b-dihydro-1-(-N-methylpyrryl)-3H-dibenz-[b,f]-oxazolo[3,4-d][1,4]oxazepin-3-one (15a);

6-chloro-1,13b-dihydro-1-(-N-methylpyrryl)-3H-dibenz-[b,f]oxazolo-[3,4-d][1,4]oxazepin-3-one (15b);

6-chloro-1,13b-dihydro-1-(4-carboxymethylphenyl)-3H-dibenz[b,f]-oxazolo[3,4-d][1,4]oxazepin-3-one (16);

6-chloro-1,13b-dihydro-1-(4-carboxymethylphenyl)-3H-dibenz[b,f]-oxazolo[3,4-d][1,4]oxazepin-3-one (17);

6-chloro-1,13b-dihydro-1-(4-carboxylic acid phenyl)-3H-dibenz[b,f]oxazolo[3,4-d][1,4]-oxazepin-3-one (18);

6-chloro-1,13b-dihydro-1-(phenyl)-3-(methyl)-dibenz[b,f]-imidazolo[3,4-d][1,4-oxazepin-3-one (19);

6-Chloro-1,13b-dihydro-1-[2,4,6-trimethyl]phenyl-3H-dibenz[b,f]oxazolo[3,4-d][1,4]oxazepin-3-one (20a);

6-chloro-1,13b-dihydro-1-[2,4,6-trimethyl]-phenyl-3H-dibenz[b,f]oxazolo[3,4-d][1,4]-oxazepin-3-one (20b)

6-Chloro-1,13b-dihydro-3H-spiro[dibenz[b,f]oxazolo[3,4-d][1,4]oxazepin-1,1'-cyclobutan]-3-one (21);

6-Chloro-1,13b-dihydro-3H-spiro[dibenz[b,f]-oxazolo[3,4-d][1,4]oxazepin-1,1'-cyclopentan]-3-one (22)

6-Chloro-1,13b-dihydro-3H-spiro[dibenz[b,f]-oxazolo[3,4-d][1,4]oxazepin-1,1'-cyclohexan]-3-one (23);

6-Chloro-1,13b-dihydro-3H,9'H-spiro[dibenz[b,f]-oxazolo-[3,4-d][1,4]oxazepin-1,9'-fluoren]-3-one (24);

6-Chloro-1,13b-dihydro-3H-spiro[dibenz[b,f]oxazolo-[3,4-d][1,4]oxazepin-1,2'-indan]-3-one (25);

6-Chloro-1,13b-dihydro-3H-spiro[dibenz[b,f]oxazolo-[3,4-d][1,4]oxazepin-1,1'-indan]-3-one (26a);

6-Chloro-1,13b-dihydro-3H-spiro[dibenz[b,f]-oxazolo[3,4-d][1,4]oxazepin-1,1'-indan]-3-one (26b );

6-Chloro-1,1°,2',3',4'-13b-hexahydro-3H-spiro[dibenz-[b,f]oxazolo[3,4-d][1,4]oxazepin-1,1'-naphthalen]-3-one (27a);

6-Chloro-1,1',2',3',4'-13b-hexahydro-3H-spiro-[dibenz[b,f]oxazolo[3,4-d][1,4]oxazepin-1,1'-naphthalen]-3-one (27b);

12-Chloro-15H-benz[b]isoquino[2',1':3,4]imidazo-[1,5-d][1-4]benzoxazepin-15-one (28);

12-Chloro-17,18-dihydro-15H-benz[b]isoquino-[2',1':3,4]imidazo[1,5-d][1,4]-benzoxazepin-15-one (29);

6-Chloro-1-phenyl-2H-dibenz[b,f]imidazo[1,5-d]-[1,4]oxazepin-3-one (30);

6-Chloro-2-methyl-1-phenyl-2H-dibenz[b,f]imidazo-[1,5-d][1,4]oxazepin-3-one (31);

6-Chloro-2-phenyl-2,13bH-dibenz[b,f]imidazo-[1,5-d][1,4]oxazepin-1,3-dione (33);

6-Chloro-2-(phenylmethyl)-2H,13bH-dibenz[b,f]-imidazo[1,5-d][1,4]oxazepin-1,3-dione (34); or 6-Chloro-2-(2-phenylethyl)-2H,13bH-dibenz[b,f]-imidazo[1,5-d][1,4]oxazepin-1,3-dione (35).

28. The method of claim 27 wherein the compound is:

trans-6-chloro-1,13b-dihydro-1-(4-pyridyl)-3H-dibenz-[b,f]oxazolo[3,4-d][1,4]oxazepin-3-one (6);

(−)-trans-6-chloro-1,13b-dihydro-1-(4-pyridyl)-3H-dibenz[b,f]oxazolo-[3,4-d][1,4]-oxazepin-3-one (6b); or cis-6-chloro-1,13b-dihydro-1-(4-pyridyl)-3H-dibenz-[b,f]oxazolo-[3,4-d][1,4]oxazepin-3-one (7).

* * * * *